(12) United States Patent
Miller et al.

(10) Patent No.: US 12,144,757 B2
(45) Date of Patent: Nov. 19, 2024

(54) ADJUSTABLE TENSIONING DEVICE

(71) Applicant: Icarus Medical, LLC, Charlottesville, VA (US)

(72) Inventors: Philip Miller, Charlottesville, VA (US); David T. Johnson, Charlottesville, VA (US); Evan Eckersley, Charlottesville, VA (US)

(73) Assignee: Icarus Medical, LLC, Charlottesville, VA (US)

( * ) Notice: Subject to any disclaimer, the term of this patent is extended or adjusted under 35 U.S.C. 154(b) by 0 days.

(21) Appl. No.: 18/387,433

(22) Filed: Nov. 6, 2023

(65) Prior Publication Data
US 2024/0065870 A1    Feb. 29, 2024

Related U.S. Application Data

(60) Continuation of application No. 18/075,203, filed on Dec. 5, 2022, now Pat. No. 11,806,264, which is a continuation-in-part of application No. 17/902,683, filed on Sep. 2, 2022, now Pat. No. 11,612,506, and a continuation-in-part of application No. 17/864,675, filed on Jul. 14, 2022, and a continuation-in-part of application No. PCT/US2022/021822, filed on Mar. 24, 2022, said application No. 17/864,675 is a continuation-in-part of application No. 17/700,479, filed on Mar. 21, 2022, now Pat. No. 11,458,034, which is a continuation-in-part of application No. 17/537,476, filed on Nov. 29, 2021, now Pat. No. 11,666,472, said application No. 17/902,683 is a
(Continued)

(51) Int. Cl.
*A61F 5/01*    (2006.01)

(52) U.S. Cl.
CPC .... *A61F 5/0125* (2013.01); *A61F 2005/0139* (2013.01); *A61F 2005/0165* (2013.01)

(58) Field of Classification Search
CPC ............ A61F 5/0125; A61F 2005/0139; A61F 2005/0165; A61F 13/048; A61F 13/107; A61F 2013/49096; A61F 5/01; A61F 5/026; A61F 5/028; A61F 2/30; A61F 2002/30624
See application file for complete search history.

(56) References Cited

U.S. PATENT DOCUMENTS 4,433,456 A    2/1984 Baggio
4,748,726 A    6/1988 Schoch
(Continued)

FOREIGN PATENT DOCUMENTS

ES    2269373 T3 *    4/2007   ........... A61F 5/0125
WO    WO-2007107150 A1 *    9/2007   ............... A61F 2/64
(Continued)

OTHER PUBLICATIONS

Fitgo Quick Lacing System product information as downloaded Jan. 11, 2023; http://en.fitgotech.com/.
(Continued)

*Primary Examiner* — Tarla R Patel
(74) *Attorney, Agent, or Firm* — Woods Rogers Vandeventer Black PLC; Nathan A. Evans

(57) ABSTRACT

An adjustable tensioning device capable of providing and holding high tensions needed for medical devices, prosthetics, and orthotics.

27 Claims, 26 Drawing Sheets

Related U.S. Application Data continuation of application No. 17/211,590, filed on Mar. 24, 2021, now Pat. No. 11,135,081, said application No. 17/537,476 is a continuation-in-part of application No. 17/211,635, filed on Mar. 24, 2021, now Pat. No. 11,819,436, and a continuation-in-part of application No. 17/074,571, filed on Oct. 19, 2020, said application No. 17/211,635 is a continuation of application No. 17/074,542, filed on Oct. 19, 2020, now Pat. No. 11,564,824, said application No. 18/075,203 is a continuation-in-part of application No. PCT/US2020/047904, filed on Aug. 26, 2020, said application No. 17/074,571 is a continuation-in-part of application No. 15/585,968, filed on May 3, 2017, now Pat. No. 10,806,619, said application No. 17/074,542 is a division of application No. 15/585,968, filed on May 3, 2017, now Pat. No. 10,806,619.

(60) Provisional application No. 63/394,530, filed on Aug. 2, 2022, provisional application No. 62/331,315, filed on May 3, 2016.

(56) References Cited

U.S. PATENT DOCUMENTS

| | | |
|---|---|---|
| 4,790,081 A | 12/1988 | Benoit et al. |
| 4,870,723 A | 10/1989 | Pozzobon et al. |
| 5,341,583 A | 8/1994 | Hallenbeck |
| 5,600,874 A | 2/1997 | Jungkind |
| 5,606,778 A | 3/1997 | Jungkind |
| 5,638,588 A | 6/1997 | Jungkind |
| 5,934,599 A | 8/1999 | Hammerslag |
| 6,289,558 B1 | 9/2001 | Hammerslag |
| 7,591,050 B2 | 9/2009 | Hammerslag |
| 7,950,112 B2 | 5/2011 | Hammerslag et al. |
| 7,954,204 B2 | 6/2011 | Hammerslag et al. |
| 7,992,261 B2 | 8/2011 | Hammerslag et al. |
| 8,091,182 B2 | 1/2012 | Hammerslag et al. |
| 8,157,691 B2 | 4/2012 | Stanovskoy et al. |
| 8,277,401 B2 | 10/2012 | Hammerslag et al. |
| 8,308,098 B2 | 11/2012 | Chen |
| 8,381,362 B2 | 2/2013 | Hammerslag et al. |
| 8,424,168 B2 | 4/2013 | Soderberg et al. |
| 8,468,657 B2 | 6/2013 | Soderberg et al. |
| 8,516,662 B2 | 8/2013 | Goodman et al. |
| 8,713,820 B2 | 5/2014 | Kerns et al. |
| 8,984,719 B2 | 3/2015 | Soderberg et al. |
| 9,101,181 B2 | 8/2015 | Soderberg et al. |
| 9,113,998 B2 | 8/2015 | Romo |
| 9,125,455 B2 | 9/2015 | Kerns et al. |
| 9,138,030 B2 | 9/2015 | Soderberg et al. |
| 9,149,089 B2 | 10/2015 | Cotterman et al. |
| 9,179,729 B2 | 11/2015 | Cotterman et al. |
| 9,248,040 B2 | 2/2016 | Soderberg et al. |
| 9,259,056 B2 | 2/2016 | Soderberg et al. |
| D751,281 S | 3/2016 | Nickel et al. |
| 9,339,082 B2 | 5/2016 | Hammerslag et al. |
| D758,061 S | 6/2016 | Whewell |
| 9,375,053 B2 | 6/2016 | Burns et al. |
| 9,408,437 B2 | 8/2016 | Goodman et al. |
| D767,269 S | 9/2016 | Lovett et al. |
| 9,439,477 B2 | 9/2016 | Neiley |
| 9,516,923 B2 | 12/2016 | Capra et al. |
| D776,421 S | 1/2017 | Venturini |
| 9,532,626 B2 | 1/2017 | Lovett et al. |
| 9,572,705 B2 | 2/2017 | Ingimundarson et al. |
| 9,610,185 B2 | 4/2017 | Capra et al. |
| 9,629,417 B2 | 4/2017 | Cavanagh et al. |
| 9,681,705 B2 | 6/2017 | Trudel et al. |
| 9,700,101 B2 | 7/2017 | Lovett et al. |
| 9,706,814 B2 | 7/2017 | Converse et al. |
| 9,737,115 B2 | 8/2017 | Soderberg et al. |
| 9,743,714 B2 | 8/2017 | Hammerslag et al. |
| 9,763,808 B2 | 9/2017 | Jonsson |
| 9,770,070 B2 | 9/2017 | Cotterman et al. |
| D799,810 S | 10/2017 | Mayberry |
| 9,854,873 B2 | 1/2018 | Kerns et al. |
| 9,867,430 B2 | 1/2018 | Hammerslag et al. |
| 9,872,568 B2 | 1/2018 | Capra et al. |
| 9,872,790 B2 | 1/2018 | Capra et al. |
| 10,004,297 B2 | 6/2018 | Lovett |
| 10,039,348 B2 | 8/2018 | Cavanagh et al. |
| 10,070,695 B2 | 9/2018 | Burns et al. |
| 10,076,160 B2 | 9/2018 | Burns et al. |
| 10,123,589 B2 | 11/2018 | Soderberg et al. |
| D835,898 S | 12/2018 | Lovett |
| D835,976 S | 12/2018 | Nickel et al. |
| 10,251,451 B2 | 4/2019 | Converse et al. |
| 10,327,513 B2 | 6/2019 | Soderberg et al. |
| 10,342,294 B2 | 7/2019 | Lovett et al. |
| 10,362,836 B2 | 7/2019 | Hammerslag et al. |
| 10,413,019 B2 | 9/2019 | Soderberg et al. |
| 10,433,999 B2 | 10/2019 | Hammerslag et al. |
| 10,477,922 B2 | 11/2019 | Lovett et al. |
| 10,492,568 B2 | 12/2019 | Burns et al. |
| 10,499,709 B2 | 12/2019 | Pollack et al. |
| 10,543,630 B2 | 1/2020 | Hipwood et al. |
| 10,575,591 B2 | 3/2020 | Schum et al. |
| 10,702,409 B2 | 7/2020 | Burns et al. |
| RE48,215 E | 9/2020 | Neiley |
| 10,772,384 B2 | 9/2020 | Whewell et al. |
| 10,772,388 B2 | 9/2020 | Burns et al. |
| D897,661 S | 10/2020 | Nickel |
| 10,791,798 B2 | 10/2020 | Lovett |
| 10,842,230 B2 | 11/2020 | Pollack et al. |
| 10,849,390 B2 | 12/2020 | Hammerslag et al. |
| 10,863,796 B2 | 12/2020 | Soderberg et al. |
| 10,888,139 B2 | 1/2021 | Burns et al. |
| 10,918,502 B2 | 2/2021 | Mahon |
| 10,952,503 B2 | 3/2021 | Trudel et al. |
| 10,952,505 B2 | 3/2021 | Hammerslag et al. |
| 10,959,492 B2 | 3/2021 | Converse et al. |
| D926,457 S | 8/2021 | Swanson |
| D926,458 S | 8/2021 | Swanson et al. |
| 11,089,837 B2 | 8/2021 | Pollack et al. |
| D932,176 S | 10/2021 | Swanson et al. |
| 11,220,030 B2 | 1/2022 | Hipwood et al. |
| 11,253,028 B2 | 2/2022 | Lovett et al. |
| 11,297,903 B2 | 4/2022 | Soderberg et al. |
| RE49,092 E | 6/2022 | Neiley et al. |
| 11,357,279 B2 | 6/2022 | Cotterman |
| 11,419,389 B2 | 8/2022 | Pollack et al. |
| 11,452,342 B2 | 9/2022 | Hammerslag et al. |
| D965,257 S | 10/2022 | Hammerslag et al. |
| 11,457,698 B2 | 10/2022 | Burns et al. |
| 11,492,228 B2 | 11/2022 | Kruse et al. |
| D971,562 S | 12/2022 | Hipwood et al. |
| 2002/0095750 A1 | 7/2002 | Hammerslag |
| 2014/0257156 A1 | 9/2014 | Capra et al. |
| 2015/0007422 A1* | 1/2015 | Cavanagh ............ A43C 11/165 29/434 |
| 2018/0152076 A1 | 5/2018 | Alei et al. |
| 2020/0346888 A1* | 11/2020 | Kruse ................ A43B 23/0205 |
| 2021/0022451 A1 | 1/2021 | Beers et al. |
| 2021/0177098 A1 | 6/2021 | Trudel et al. |
| 2021/0251343 A1 | 8/2021 | Martin et al. |
| 2022/0175089 A1 | 6/2022 | Pollack et al. |

FOREIGN PATENT DOCUMENTS

| | | |
|---|---|---|
| WO | 2014036471 A2 | 3/2014 |
| WO | 2014071319 A1 | 5/2014 |
| WO | 2014074645 A2 | 5/2014 |

OTHER PUBLICATIONS

Uturn Smart Lacing System product information as downloaded Jan. 11, 2023; https://uturn.eu/.

Youxiang Automatic Shoelace product information as downloaded Jan. 12, 2023; https://www.walmart.com/ip/Automatic-Shoelace-Fast-Automatic-Shoelace-Artifact-For-Lazy-People-Camping-

(56) References Cited

OTHER PUBLICATIONS

Accessories/1831795014?wmlspartner=wlpa&selectedSellerId=101124324&adid=22222222227000000000&wl0=&wl1=g&wl2=c&wl3=42423897272&wl4=aud-393207457166:pla-51320962143&wl5=9008336&wl6=&wl7=&wl8=&wl9=pla&wl10=537182653&wl11=nline&wl12=1831795014&veh=sem&gclid=EAIaIQobChMIseTJyZrC_AIVGYvlCh0QIQykEAQYASABEgLXUfD_BwE.

Application No. PCT/US 23/82610, International Search Report and Written Opinion dated May 10, 2024.

* cited by examiner

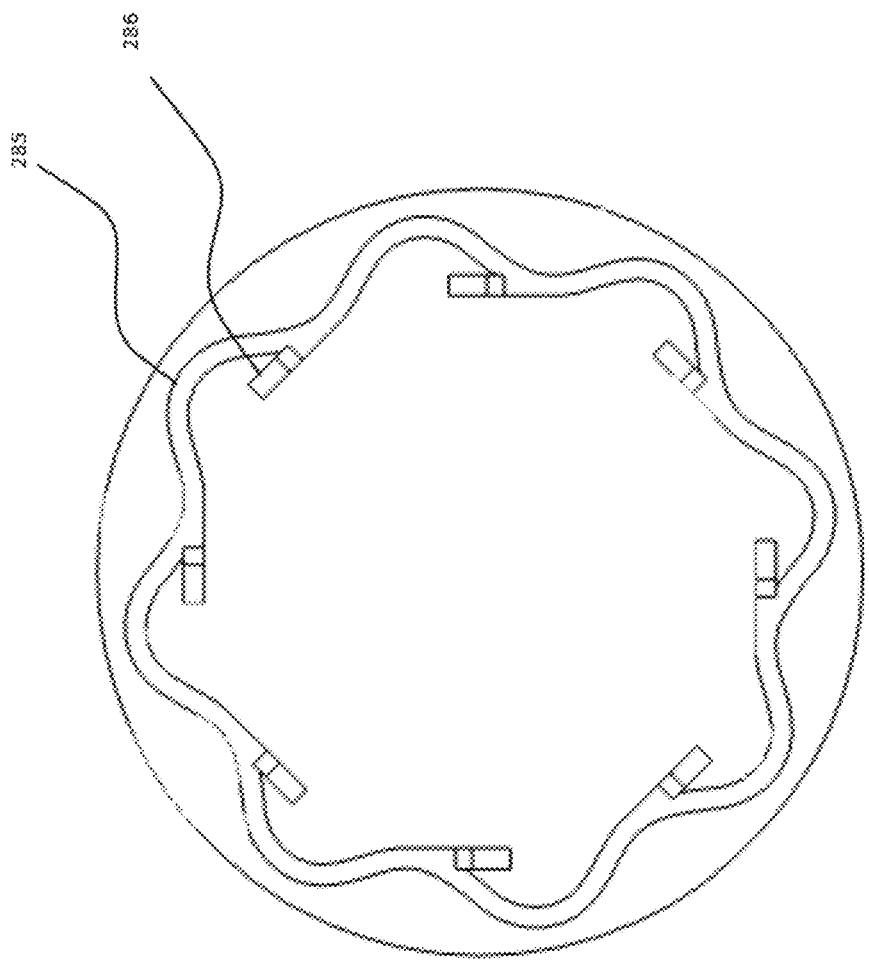
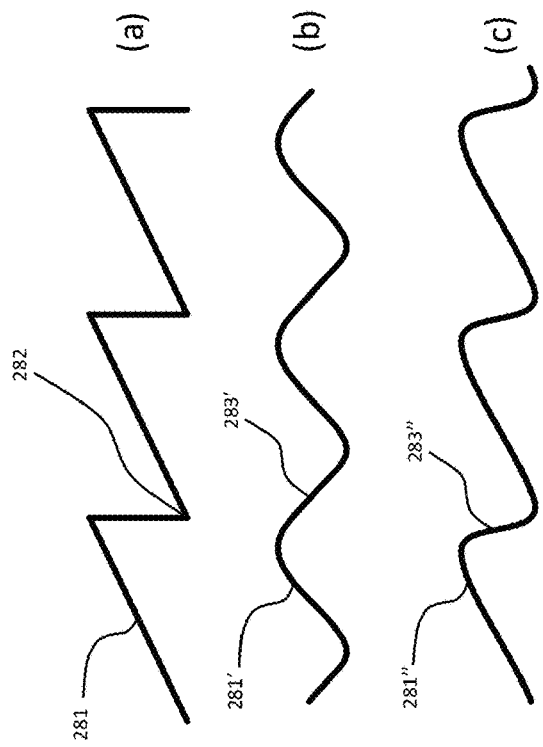
Figure 28a
Figure 28b

ADJUSTABLE TENSIONING DEVICE

CROSS-REFERENCE TO RELATED APPLICATIONS

The present application is a child application of and relies on the disclosures of and claims priority to and the benefit of the filing dates of the following, and the disclosures of the following applications and other applications/patents/literature cited herein are hereby incorporated by reference herein in their entirety:
U.S. patent application Ser. No. 18/075,203, filed Dec. 5, 2023,
U.S. patent application Ser. No. 17/902,683, filed Sep. 2, 2022,
U.S. patent application Ser. No. 17/864,675, filed Jul. 14, 2022,
U.S. patent application Ser. No. 17/700,479, filed Mar. 21, 2022,
U.S. patent application Ser. No. 17/537,476, filed Nov. 29, 2021,
U.S. patent application Ser. Nos. 17/211,590 and 17/211,635 filed Mar. 24, 2021,
U.S. patent application Ser. Nos. 17/074,571 and 17/074,542, filed Oct. 19, 2020,
U.S. patent application Ser. No. 15/585,968 filed May 3, 2017,
U.S. Provisional Patent Application No. 62/331,315 filed on May 3, 2016,
PCT Application No. PCT/US2020/047904, filed Aug. 26, 2020,
PCT Application No. PCT/US2022/021822, filed Mar. 24, 2022, and
U.S. Provisional Patent Application No. 63/394,530, filed Aug. 2, 2022.

BACKGROUND OF THE INVENTION

Field of the Invention

The current invention comprises a tensioning device capable of high tensions needed for medical prosthetics and orthotics, as described herein.

Description of Related Art

Dial tensioning systems are used for apparel and sports equipment to adjust the fit of the equipment to the wearer. Dial tensioning systems made by BOA Technologies of Colorado, USA; YOW Systems of the YouNing Technology Company located in Shenzhen, China; FitGo Technology located in Shenzhen, China; UTurn located in Soeborg, Denmark; and Fidlock Gmbh located in Hannover, Germany, are used on snowboarding boots, bicycle safety helmets, and athletic shoes, for example. In such examples, a lace connects two opposing elements of the apparel. Turning the dial tensioning system draws the two opposing elements closer together thereby tightening the apparel to the wearer's body. Such systems are described in the prior art as "closure systems," "closure device[s]," or "lacing systems," which are fundamentally different functionally from the current invention to a high-torque tensioning device for adjusting forces around, across, or between a joint or body part.

The amount of tension that the dial must produce in these examples is relatively low. For example, the spring constant of common elastic athletic shoelaces made by LockLaces was measured to be 0.8 lbs/in. It is reasonable that the amount of tension needed to secure footwear is about 1-2 lbs. of tension.

A study on the Twisting Force of Aged Consumers When Opening a Jar published in the journal of Applied Ergonomics in February 2002, recommends a torque of ~18 in-lbs. or less for consumers 50 to 94 years of age. A table of torque guidelines for bottle caps published on https://www.kinexcappers.com/faq/torque-guidelines.htm recommends a torque of 10-18 in-lbs. for caps ~1" in diameter. This is roughly the same magnitude for the tension needed to secure footwear.

In practice this means that dial tensioning systems for foot wear do not require large torque multipliers. An average user has enough wrist strength to tighten footwear by turning a dial with a 1:1 torque multiplier. Moderate torque multiplying methods—for example, designing the dial with a larger diameter than the winding shaft—are sufficient for many apparel applications.

The BOA Technologies website lists four different basic dial platforms—the H-series, the M-series, the S-series, and the L-series—of which three series do not employ a torque multiplier system (other than the dial/shaft diameter difference mentioned above). FitGo lists 17 different dial styles on their website within the L2 Series, the M5 Series, the L7 Series, and the L8 Series. None of the FitGo dials employ a torque multiplier system (other than the dial/shaft diameter difference). Likewise, neither FidLock nor YOW Systems offer torque multiplier systems on any of their models (other than the dial/shaft diameter difference.)

The BOA Technologies H4 dial style uses a planetary gear multiplier system which contributes approximately a 4:1 mechanical advantage. However, the anti-unspooling feature used in the H4 dial is a series of backwards angled dogs at roughly a 45 degree angle. The H4 dial is released by pulling the dial upwards which disengages the dial from the dogs. As the tension on the dial is increased, the resulting force pressing the dial into the body of the dial tensioning element increases. That is, for every pound of winding tension about 0.7 lbs. of force presses the dial into the body of the H4 dial tensioning device. For typical footwear tensions, this means the user would need to pull the dial upwards with ~0.7-1.4 lbs. to release it. As the amount of tension that is applied by the BOA H4 dial tensioning system increases, the force needed to pull up the dial to release it also increases. It follows that beyond a certain point, the force needed to release the dial will exceed the average hand strength of the user. This is especially a problem for elderly users.

For applications where the total tension is (relatively) low and where the user population is young and fit (e.g., sports equipment users), this design limitation is not an issue. For other applications that require relatively high tensions, an older population of users, and/or users with a medical condition that affects strength or agility, the design tradeoffs of the BOA H4 is not a currently adequate solution, a problem which is resolved by the current invention.

Furthermore, it should be considered that lower limb orthotic and prosthetic devices support significant amounts of weight in the range of hundreds of pounds per limb. Existing tensioning devices do not provide the strength and durability required to reliably support these forces needed to assist gait, immobilize a joint, or replace the normal function of muscles, tendons and ligaments.

SUMMARY OF THE INVENTION

In embodiments, the current invention is to a rotary tensioning device especially for, in some cases, medical devices, prosthetics and orthotics, the device capable of producing and holding high tensions, easy to use for elderly or infirm users, and having the release force remain relatively constant no matter how much tension is applied. Such a device would be suitable for generating or moderating forces across, between, or along components of medical, prosthetic or orthotic devices, to produce the relatively large forces needed for limb, joint and muscle treatment.

BRIEF DESCRIPTION OF THE DRAWINGS

FIGS. 28a and 28b depict embodiments of an adjustable tensioning device according to the invention described herein.

DETAILED DESCRIPTION OF THE INVENTION

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

All references cited in this specification are hereby incorporated by reference in their entireties.

In embodiments, the current invention comprises a tensioning device capable of high tensions needed for medical prosthetics and orthotics, as described herein, which can have several sub-elements: an anchor and socket, a spool and tension element, a clutch, an anti-unspooling mechanism, a torque multiplier system, and a dial. ("High tension," in aspects, can mean more than 100 lbs. of tension on the tension element wrapped around the spool. In other aspects, it can mean more than 50 lbs., more than 60 lbs., more than 70 lbs, and so on and so forth.) Some of the elements described herein may be sub-mechanisms with several moving pieces. In aspects, various elements or the functions of the elements may be combined to simplify the assembly of the tensioning device.

Figure 1:
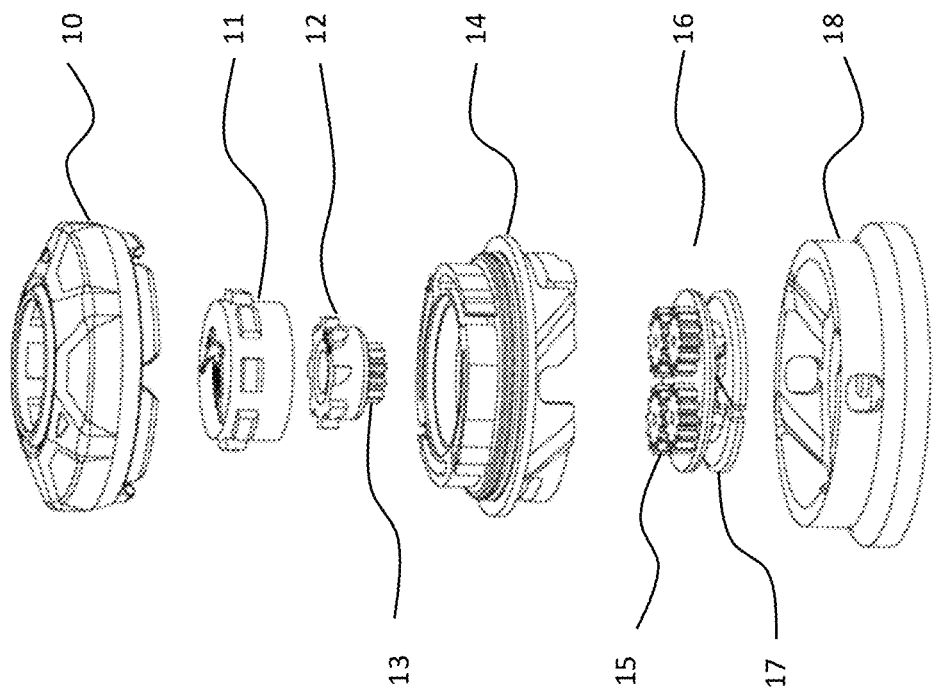
FIG. 1 depicts an embodiment of an adjustable tensioning device according to the invention described herein.

FIG. 1 shows an exploded view of a typical configuration of the invention described herein. The dial (10) snaps onto the anchor (14) and captures the release button (11) and the sun gear drive element (12) of the torque multiplier system (16). The sun gear (13) is embedded in the drive element (12). The planetary gears (15) are connected to the spool (17) and engage in corresponding teeth not visible in the anchor ring (14). The anchor ring (14) twists and locks into the socket (18). The tensioning element is not shown in FIG. 1. The clutch as described above is combined into the connection mechanism between the button (11) and the drive element (12). The anti-unspooling mechanism as described above is obtained by the interaction of the arms disposed around the anchor (14) and recesses disposed along the inner surface of the dial (not visible). The torque multiplier system example of FIG. 1 comprises two systems: a planetary gear drive which comprises the spool (17) which acts as the carriage of a planetary gear drive, planetary gears (15), the sun gear (13), and the inner ring gear (not visible in the interior of the anchor ring) (14); and the torque multiplier difference between the diameter of the dial (10) and the diameter of the shaft of the spool (17). "Tension element" as used herein can include cables, cords, braids, string, lace, thread, rope, and the like, as well as the various combinations of flexible, substantially non-elastic material that can be wrapped around the spool. "Tension element" or "tensioning element" as used herein can further include an energy storage element as described herein.

Spool and Tension Element

In embodiments, the first end of the tension element can be connected to the element of the orthotic or prosthetic that requires tensioning. The second end of the tension element can be connected to the spool. In aspects, another element of the orthotic may require tensioning. A second tension element may be employed to connect this second element to the spool. Alternatively, a single tension element connects the two orthotic elements and passes through or is attached to the spool such that as tension element is collected on the spool, both orthotic elements are tensioned. In another aspect, a second end of the tension element is attached to a non-tensioning element of an orthotic (for example, an anchoring element) and passes through or is attached to the spool. In aspects described above, as the spool is rotated it winds the tension element around itself.

The dimensions of the spool can, in aspects, affect the performance of the tensioning device. The channel or receptacle in the spool that gathers the tension element needs to be large enough to hold all the tension element that needs to be wound. The size of the channel or receptacle depends on the diameter of the tension element, the length that will be wound, and/or the number of tension elements connected to the spool. A thinner diameter tension element is advantageous, in aspects, because a longer length of tension element can be collected in the channel or receptacle. On the other hand, a thinner diameter tension element typically has less tensile strength than a thicker diameter tension element. In addition, a thinner diameter tension element can cut into the spool at high tensions. Suitable tension element materials and diameters for the tensioning device described herein can be, in aspects, ultra-high molecular weight polyethylene (UHMWPE), polyester, Kevlar, aircraft cable, and the like, between, by way of example, 0.5 mm and 3 mm in diameter.

In embodiments, the diameter of the spool can define or determine the depth of the channel or receptacle. A deeper channel, that is—a smaller spool diameter—can store more of the tension element. In addition, a small diameter spool combined with a large diameter dial adds to the torque multiplier effect. However, as the spool diameter gets smaller, the tension on the tension element can cut into the spool material thereby causing failure. Experimental trials of commercially available spools made of polypropylene with a diameter of 14 mm failed when the tension was applied to a UHMWPE tension element with a diameter of 1.2 mm. In another trial of several, the tension element cut through the spool at 160 lbs. of tension; in yet another trial, the tension element cut through the spool at 200 lbs. of tension. Experiments of spools made of 3D printed nylon 12 were able to withstand tension element tensions of 200 lbs. without failure when the spool diameter was 18 mm or greater.

Figure 2B:
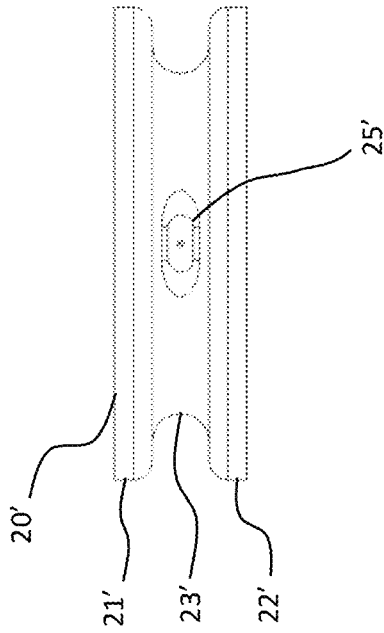
FIGS. 2a, 2b, 2c, and 2d depict aspects of an embodiment of an adjustable tensioning device according to the invention described herein.
Figure 2A:
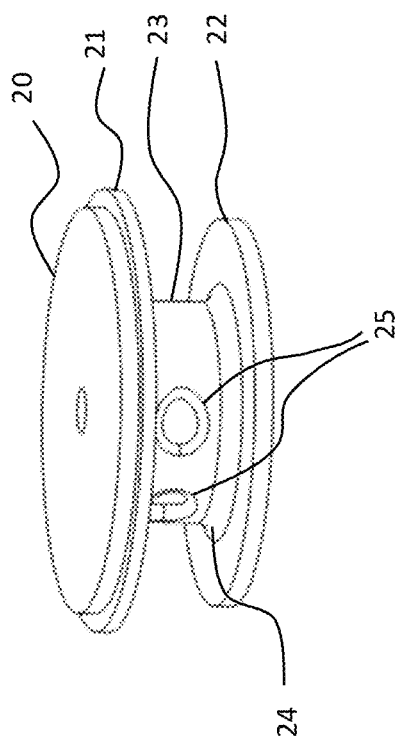

FIG. 2a shows a typical spool (20) suitable for winding the tension element (not shown) of the present invention. There is an upper flange (21) and a lower flange (22) that help capture the tension element as it winds around the shaft (23) to prevent it from tangling. In FIG. 2a, two holes (25) are positioned through the center of the shaft to be used to secure the tension element to the spool. A fillet (24) is provided to oppose the tendency of the tension element from cutting into the spool. FIG. 2b shows another version of a typical spool (20'). The height of the shaft (23') and the size of the fillet (24') is such that the top and bottom fillets blend into each other for maximum resistance to cutting of the tension element. The dual holes (25) to secure the tension element shown in FIG. 2a have been replaced by a single oblong hole (25') in FIG. 2b which may be wide enough to accept two or more tension elements side by side.

In aspects, the spool can be reinforced to resist cutting by the tension element with another material (or materials) that has (or have) greater cutting resistance than the spool material itself. For example, the shaft of the spool made of polypropylene could be reinforced with a sleeve of ultra high molecular weight polyethylene, glass reinforced nylon, an epoxy/carbon fiber composite, metal tubing, a ceramic, a glass, various combinations therein, or the like. In this manner, the advantageous toughness, light weight, low cost, and shock resistance of polypropylene could be employed in the body of the spool while increasing the cutting resistance of the spool by the tensioning element at the surfaces of reinforcement. Other geometries of the reinforcing material, such as a dowel pin, could be used in conjunction with or in place of a sleeve.

Figure 2D:
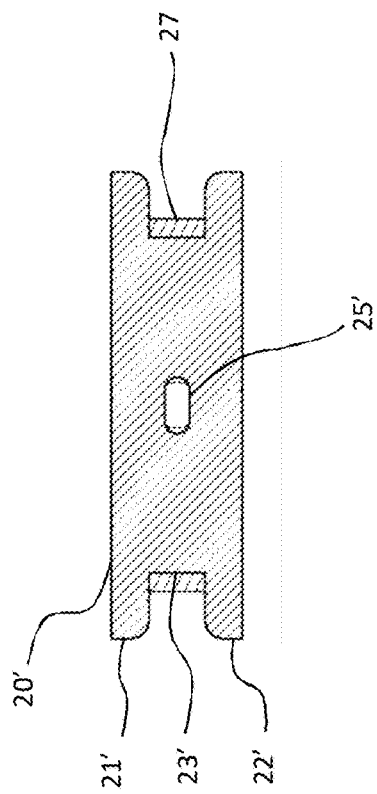
Figure 2C:
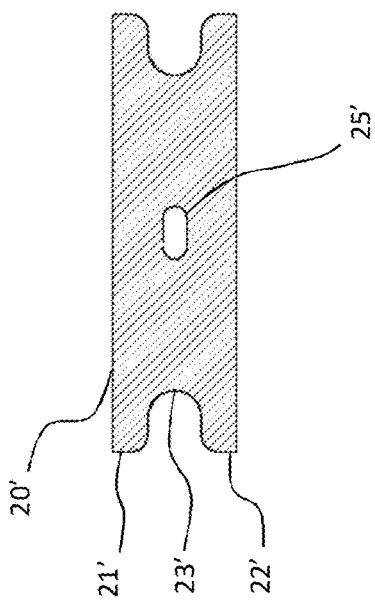

FIG. 2c is a sectional view of the spool in 2b. FIG. 2d is a sectional view of a spool variant that shows the location of a reinforcing sleeve (27).

Figure 3B:
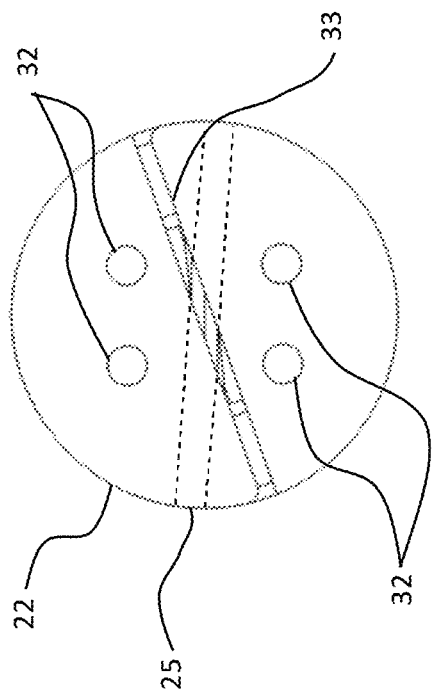
FIGS. 3a and 3b depict aspects of an embodiment of an adjustable tensioning device according to the invention described herein.
Figure 3A:
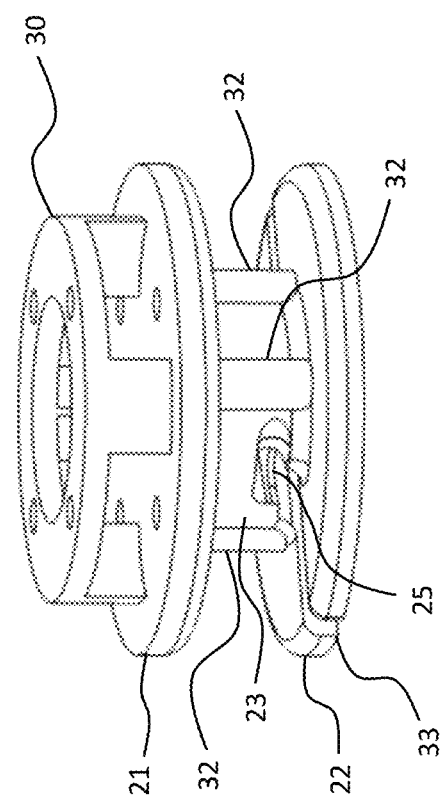

FIG. 3a is an illustration of a spool variant with an integrated planetary gear drive carriage (30). The carriage (30) is connected and integral with the top flange (21). The shaft (23) is reinforced with four dowel pins (32). In this variant, the feature to secure the tension element (25) is hole through the shaft with an offset passage (33) extending all the way through the bottom flange (22). FIG. 3b is a bottom view of the spool in FIG. 3a. The location of the dowel pins (32) are clearly shown. The path of the hole (25) through the shaft is shown by dashed lines in FIG. 3b. In other words, as shown in FIG. 3, the spool includes a spool shaft, a bottom flange, and a top flange, wherein one or more reinforcement structures are located within the spool and oriented perpendicular to the bottom flange and the top flange and parallel to the spool shaft.

Example #1

A spool with a shaft diameter of 14 mm was 3D printed out of nylon 12. The total height of the spool was 9 mm. 25 mm diameter flanges, 2 mm (thick) capped the ends of the spool to retain the wound tension element. Four holes 3 mm in diameter were formed through the entire spool from flange to flange. The distance from the center of the holes to the center of the spool was 6 mm. Four 9 mm long stainless steel dowel pins 3 mm in diameter were pressed into the holes. A portion of the cylindrical outer surface of the dowel pins protruded from the surface of the shaft. A tensioning element 1.2 mm in diameter made of UHMWPE was wound around the spool at 200 lbs of tension and then the tension was released. This was repeated ten times. At the termination of the trial, no cutting was observed on the shaft of the spool.

Attaching the tension element (or tension elements) to the spool can be accomplished by providing a hole (or holes) through the spool. The hole needs to be larger than the diameter of the tension element so the tension element can pass through it. If the diameter of the hole is too big it will reduce the strength of the spool and make it prone to cutting under tension. Fillets and chamfers can help prevent cutting of the tension element.

A method of attaching the tension element to the spool is to pass it through the hole and tie a knot in the end. The knot must be large enough so that it does not squeeze through the hole when the tension element is under tension, such as high tension. Thus, a large diameter hole to accommodate a variety of tension element diameters from 0.5 to 3 mm (for example) can make it difficult to secure smaller diameter tension elements by using a knot on one end.

A passage or slot (33) can be cut into the spool from one flange extending to the middle of the channel or receptacle such as shown in FIGS. 3a and 3b. Such a passage removes the need for threading the tensioning element though a hole aiding in the assembly of the orthotic. The slot can be a direct connection to the main tensioning element path (25), or it can be offset from the path to create a connected yet securing path for the tensioning element to prevent it from accidentally detaching from the spool.

Example #2

A spool 3D printed from nylon 12 with a diameter of 20 mm, a channel height of 4 mm, flanges 2 mm thick and 25 mm in diameter, was tested with 1.2 UHMWPE tension element. A passage 1.5 mm wide extended from the bottom flange into the spool 4 mm. A 2 mm cylinder was cut into the passage through the spool. Up to 1 meter of tension element could be wound on the spool. The spool was wound until tension on the tension element reached 200 lbs. Slight markings by the tension element were noted, but no damage was observed when the tension was released and the tension element unwound.

In embodiments, the spool described herein, represents one example of a winding element. A winding element can be defined as a component or combination of components that are capable of gathering a lace, cable, wire, elastomer or other forms of tensioning element upon rotation. Other examples of a winding element include a paddle, two or more dowels, a belt, or a combination of spools (for example in a pulley system).

Clutch

In embodiments, a functional preference of the tensioning device is that it be able to apply tension to the tension element, hold it securely, and release the tension (preferably easily release the tension). The tension can be applied by turning the dial. The tension can be held by means of the anti-unspooling mechanism (or elements). The clutch can be used to couple the spool to the anti-unspooling mechanism. In a preferred embodiment, when the clutch is engaged, the spool cannot unwind. In a preferred embodiment, when the clutch is disengaged, the spool unwinds (such as freely unwinds) thereby releasing the tension.

In embodiments, the clutch of the invention described herein has two intermeshing pieces. In one embodiment, the first clutch element comprises a plurality of protrusions that intermesh/engage with a plurality of recesses in the second clutch element. In another embodiment, the first clutch element comprises a plurality of protrusions that intermesh/engage with a plurality of protrusions on the second clutch element. The first clutch element can be attached, fixed, or built into the upper flange of the spool. The second clutch element can be attached, fixed, or built into the anti-unspooling mechanism or the torque multiplier system.

The clutch geometry can be predominately planar, cone shaped, or cylindrical. When the clutch is predominantly planar, the intermeshing elements protrude (or are sunk) from the surface (into the surface) of the first clutch element. Corresponding intermeshing elements are sunk (or protrude) into the surface (from the surface) of the second clutch element.

Figure 4B:
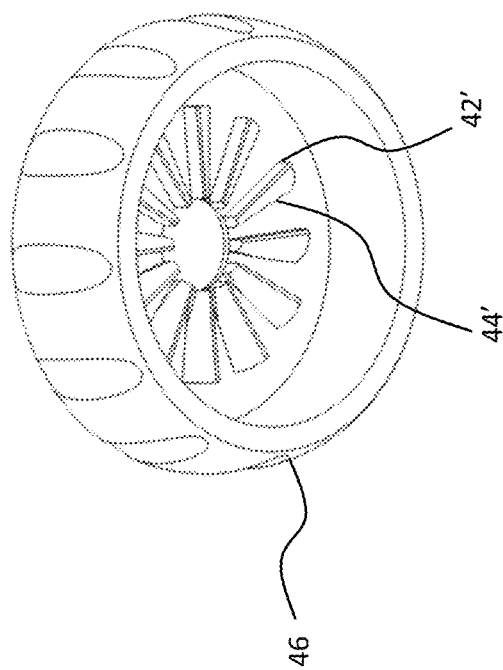
FIGS. 4a and 4b depict aspects of an embodiment of an adjustable tensioning device according to the invention described herein.
Figure 4A:
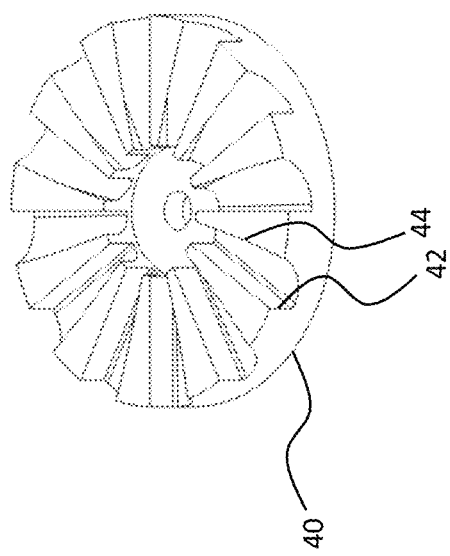

FIG. 4a is an illustration of one embodiment of a predominately planar clutch (40) with twelve identical intermeshing element features. Each feature has a leading edge (42) and a trailing edge (44). FIG. 4b is an illustration of the mating clutch piece for the one shown in FIG. 4a. In this example, the second clutch piece is built into a dial (46). There are twelve intermeshing element features that mate with the features shown in FIG. 4a. Each intermeshing feature in FIG. 4b has a leading edge (42') and a trailing edge (44').

Figure 5B:
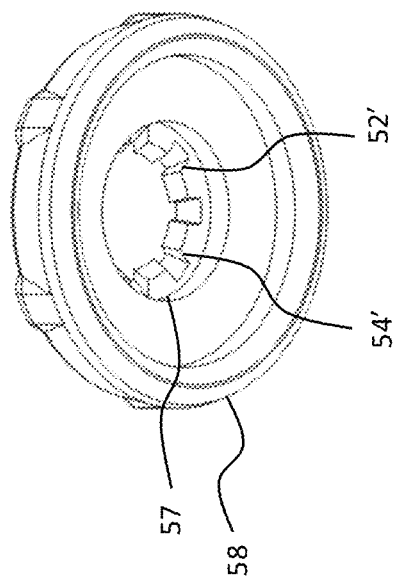
FIGS. 5a and 5b depict aspects of an embodiment of an adjustable tensioning device according to the invention described herein.
Figure 5A:
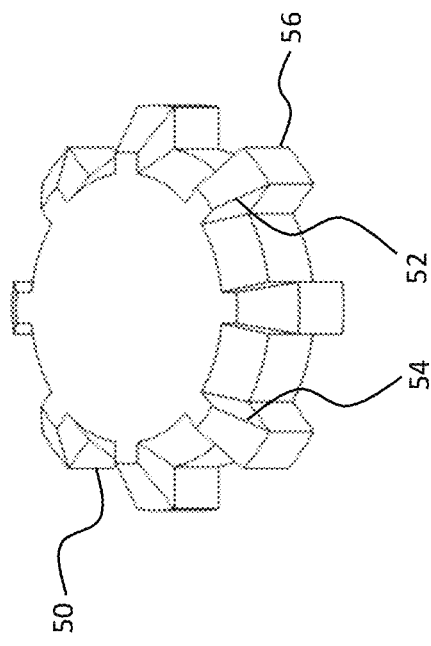

FIG. 5a is an illustration of one embodiment of a predominantly cone shaped clutch (50) with eight identical intermeshing element features. Each feature has a leading edge (52) and a trailing edge (54). The first clutch piece (50) is integrally attached to a spline feature (56) which allows the clutch piece to securely engage with dial tensioning device in both an upwards and a downwards position. In the upward position the first clutch piece (50) engages with a corresponding second clutch piece (57) that is shown in FIG. 5b as integrally attached to a dial (58). There are eight identical intermeshing element features in the second clutch piece each with a leading edge (52') and a trailing edge (54').

Figure 6B:
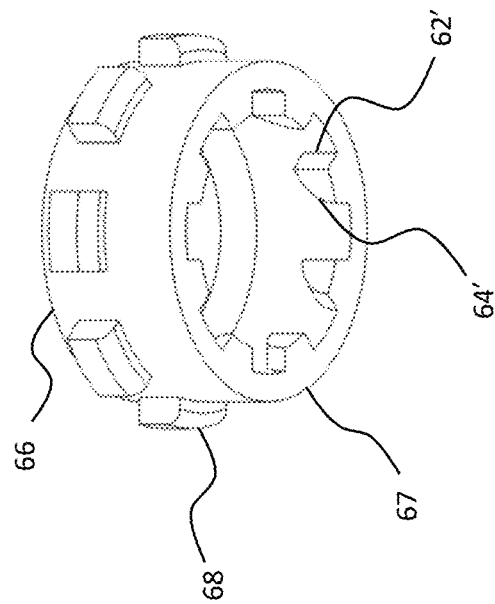
FIGS. 6a and 6b depict aspects of an embodiment of an adjustable tensioning device according to the invention described herein.
Figure 6A:
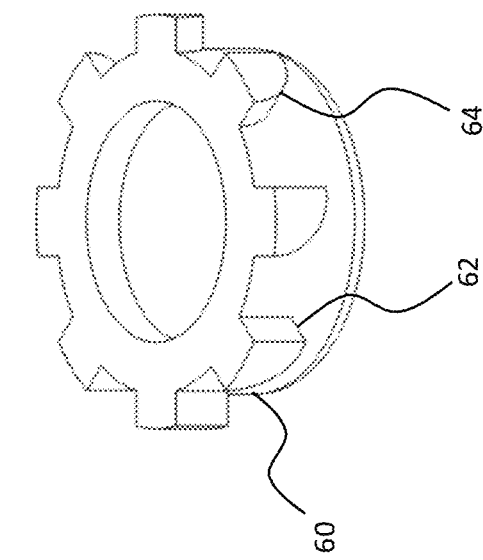

FIG. 6a is an illustration of one embodiment of a predominately cylindrical clutch (60) with eight identical intermeshing element features (e.g., protrusions). Each feature has a leading edge (or protrusion face) (62) and a trailing edge (64). FIG. 6b shows the corresponding second clutch piece (67) having recesses that mate with the protrusions of the first clutch piece shown in FIG. 6a. The second clutch piece is integrally attached to a release button (66). There are eight identical intermeshing elements each with a leading edge (62') and a trailing edge (64'). The trailing edges (64) and (64') are designed so that when the second clutch piece (67) is position downwards of the first clutch piece (60) (the disengaged mode) the intermeshing features are able to easily self-align so that the second clutch piece can move upwards (into the engaged mode). In the engaged mode, the leading edges (62) and (62') of the intermeshing elements are aligned and are fully or nearly fully in contact with each other. The splines (68) enable the release button (66) to securely engage with the dial tensioning device in both the upward (engaged) and lower (disengaged) positions.

Force is transmitted from the first clutch piece to the second clutch piece when the intermeshing elements of the first clutch piece press against the intermeshing elements of the second clutch piece. The contact surface of the first intermeshing elements with the second intermeshing elements can be planar, curvilinear, or combinations of the two. The contact surface can be normal to the force vector from the first clutch piece to the second clutch piece.

Figure 7B:
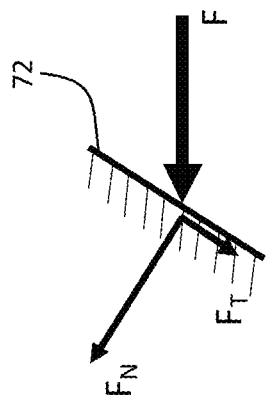
FIGS. 7a and 7b depict aspects of an embodiment of an adjustable tensioning device according to the invention described herein.
Figure 7A:
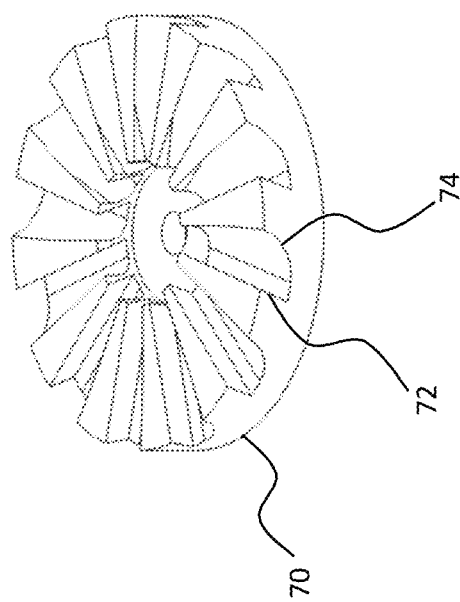

In aspects, the contact surface can be at an angle to the force vector. FIG. 7a shows a substantially planar first clutch piece (70) with twelve identical intermeshing element features, each with a leading edge (72) and a trailing edge (74). The leading edge (72) has a 20 degree back angle.

In aspects where the surface is at an angle to the tensioning force vector, the force vector can be resolved into a force normal to the intermeshing element surface and a force tangential to the intermeshing element surface. FIG. 7b shows a force diagram of the tensioning force on a schematic of the leading edge (72) of the first clutch piece. The tensioning force, F, has been resolved into two orthogonal forces: $F_N$ which is normal to the surface of the leading edge and $F_T$ which is tangential to the surface of the leading edge. When there is a tangential force vector, the tangential forces may act to drive the first clutch element into the second clutch element. Such a tangential force would advantageously help keep the first clutch element engaged securely with the second clutch element but may disadvantageously hinder the willful separation of the first clutch piece from the second clutch piece. Conversely, the tangential force can work to disengage the first clutch piece from the second clutch piece either prematurely (for a poor design) or upon reaching a predetermined maximum force (for a self-limiting clutch).

Ideally, the intermeshing elements' surfaces would not slide and disengage in an unwanted manner when a force is applied from the first clutch piece to the second clutch piece. Similarly, the force to purposely disengage the clutch pieces would be constant and not determined by the amount of tension applied by the tensioning element. Adding notches, roughness, dimples, contours and the like to the surfaces of the intermeshing elements can be used to help reduce unwanted disengagement of the first and second clutch pieces.

Figure 8B:
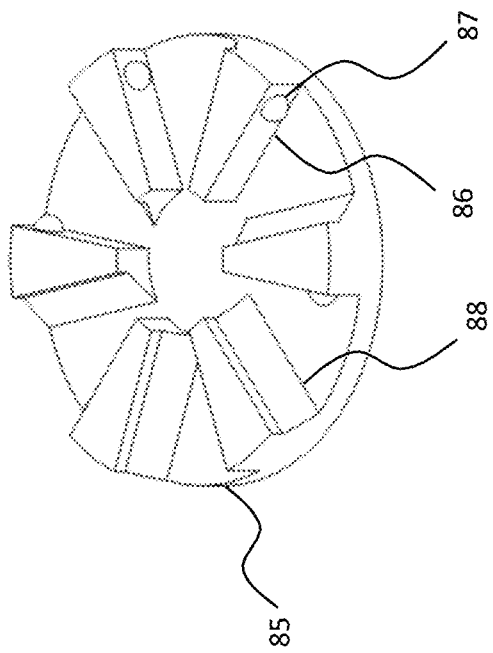
FIGS. 8a and 8b depict aspects of an embodiment of an adjustable tensioning device according to the invention described herein.
Figure 8A:
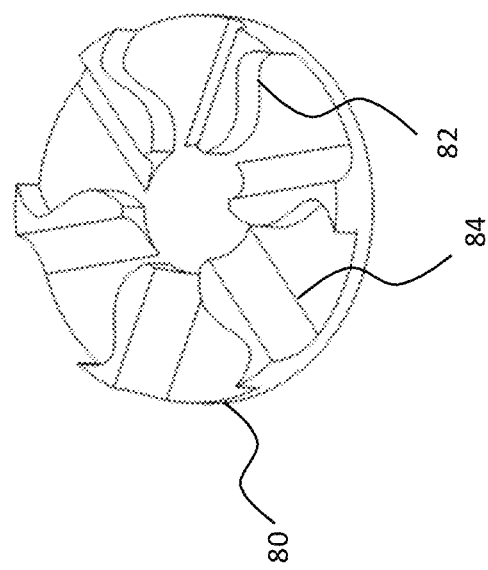

FIG. 8a is an illustration of one embodiment of a substantially planar clutch piece (80) with six identical intermeshing element features each with a leading edge (82) and a trailing edge (84). The leading edge as shown is curvilinear and provides more contact surface area with the corresponding second clutch piece (not shown). FIG. 8b is an illustration of another embodiment of a substantially planar clutch piece (85) with six identical intermeshing element features each with a leading edge (86) and a trailing edge (88). The trailing edge in FIG. 8b is depicted as a chamfer (as opposed to the filleted trailing edge in FIG. 8a). Both fillets and chamfers on the trailing edges help the first and second clutch pieces to self-align when moving from a disengaged to engaged position. A dimple (87) is shown on each intermeshing element feature which is designed to fit with a corresponding recess in the second clutch piece (not shown).

The portions of the clutch pieces upon which the intermeshing elements are attached should not flex excessively when a force is applied from the first clutch piece to the second clutch piece. If the clutch piece can flex too much, the angle between the intermeshing element surface normal and the force vector may increase to the point where the tangential force vector catastrophically disengages the first and second clutch pieces.

A predominately cone shaped clutch piece and a predominately cylindrically shaped clutch piece are less prone to flexing than a predominately planar clutch piece. However, cone shaped and cylindrically shaped clutch pieces are taller than planar clutch pieces and may not be as desirable when a compact clutch is desirable.

Flexing can be countered by reinforcing the clutch piece with a stiff material such as a composite, glass, ceramic, or metal. Likewise wear of the sliding faces of the intermeshing element surfaces can be reduced by reinforcing, coating, or impregnating the surfaces with suitable materials.

Example #3

A predominately or substantially planar first clutch piece was 3D printed from nylon 12 and incorporated into the upper flange of a spool. The diameter of the first clutch piece was 25 mm. Twelve wedge elements protruded from the upper flange spaced equally around the circumference of the spool flange. Each wedge was 2 mm tall with a 15 degree arc in the circumferential direction. A 25 degree draft was incorporated on the trailing face of the 12 wedges. (In this example, the counterclockwise direction of the wedge was the trailing face.) The leading face of all the wedges were 90 degrees from the plane of the upper flange surface.

A second clutch piece was 3D printed from nylon 12. The second clutch piece had a face that was the geometrical reciprocal of the first clutch piece face. (In this application, 'geometric reciprocal' is defined as the boolean combination of two geometries where one geometry is removed from the other geometry. Thus, where the wedges protruded from the spool flange in the first clutch piece, a corresponding wedge shape was cut out of the face of the second clutch piece.) A 0.5 mm relief was cut from the trailing draft faces of the second clutch piece wedges to enable the first clutch piece and the second clutch piece to nest.

A spring with 4 lbs. of compression strength pressed on the bottom face of the spool thereby forcing the first clutch piece to engage with the second clutch piece.

A tension element was attached to the spool and the spool was wound in a clockwise direction to increase the tension on the tension element. The tension on the tension element was measured. When the tension element tension exceeded 120 lbs. of tension, the first clutch piece disengaged from the second clutch piece causing the spool to unwind.

Example #4

A spool was 3D printed from nylon 12 with an 18 mm diameter, 25 mm diameter flanges, where the spool channel was 5 mm tall and each flange was 1 mm tall. A first clutch piece was 3D printed into the upper flange face. The first clutch piece was 25 mm in diameter. Twelve wedges were spaced equally, radially around the circumference. The wedges were 2 mm tall with a 15 degree arc length. The trailing edge of each wedge was given a 25 degree draft. The front edge of each wedge was 90 degrees from the face of the flange.

A second clutch piece was 3D printed from nylon 12. The second clutch piece was the geometrical reciprocal of the first clutch piece. A 0.5 mm relief was cut from the trailing draft faces of the second clutch piece wedges to enable the first clutch piece and the second clutch piece to nest.

When the spool was wound, generating a tension on the element tension of >100 lbs., the upper flange of the spool broke at the stress concentration corner of one of the first clutch piece wedges.

Example #5

A predominately cylindrical first clutch piece was 3D printed from nylon 12. The outer diameter was 12 mm with an inner diameter of 10 mm and a height of 7 mm. Eight intermeshing elements 2.5 mm long circumferentially by 1.5 mm long radially by 3 mm tall were arranged uniformly around the top outer edge of the cylinder. The bottom, trailing edges of each intermeshing element was fileted with a 3 mm radius.

A second cylindrical clutch piece was 3D printed from nylon 12. The outer diameter was 20 mm with an inner diameter of 18 mm. Eight intermeshing elements 1.5 long radially and 3 mm tall were arranged uniformly along the bottom inner edge of the cylinder. The top, trailing edges of each intermeshing element was fileted with a 3 mm radius.

The intermeshing elements were fully engaged when the bottom edge of the second clutch piece was 3 mm below the top edge of the first clutch piece. A spring with a compression force of 10 lbs at full compression was placed between the first and second clutch pieces.

Figure 19:
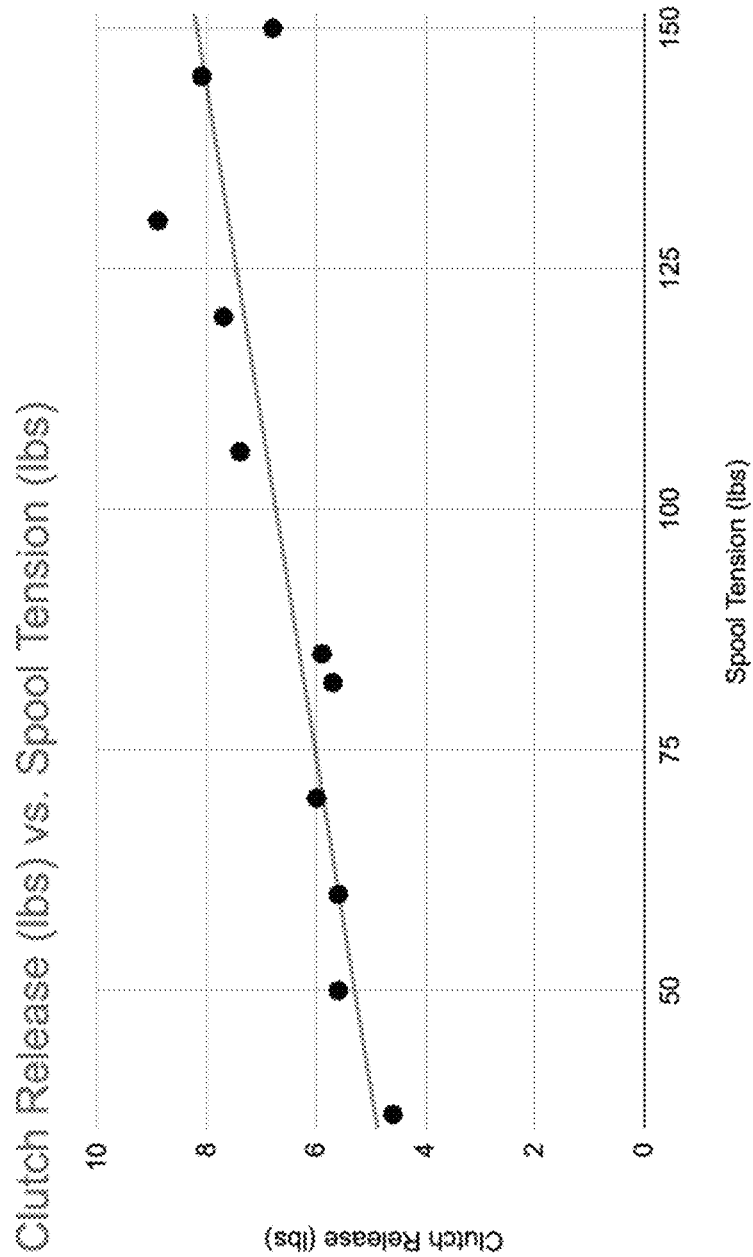
FIG. 19 is a chart showing various aspects of the invention as described herein.

Torque applied to the second clutch piece was transmitted via a planetary gear system to a spool via the first clutch piece. Different values of tension were applied to the tension element wrapped around the spool and the force to slide the second clutch piece down to disengage it from the first clutch piece. FIG. 19 shows a graph of the force to disengage the clutch versus the tension applied to the spool. The trend line in FIG. 19 is generally flat with the majority of the values lying between 4 and 8 lbs. This result is surprisingly advantageous because it means that the force needed to allow the spool to unwind does not increase dramatically with the amount of tension applied to the tension element. Also, the magnitude of the force is low which means that this clutch mechanism is very suitable for applications for the elderly, infirm, children, or injured people.

In addition, the release motion of the clutch in this example was a downward push. Pushing a button, dial, or boss is preferred as a release mechanism for a dial tensioning device compared to pulling. Pulling a dial (for example) requires grasping strength that may be beyond the capabilities of the elderly, infirm, children, or injured people. This push-button release also solves problems with currently available on-market technologies that are likely to jam and fail.

Figure 20:
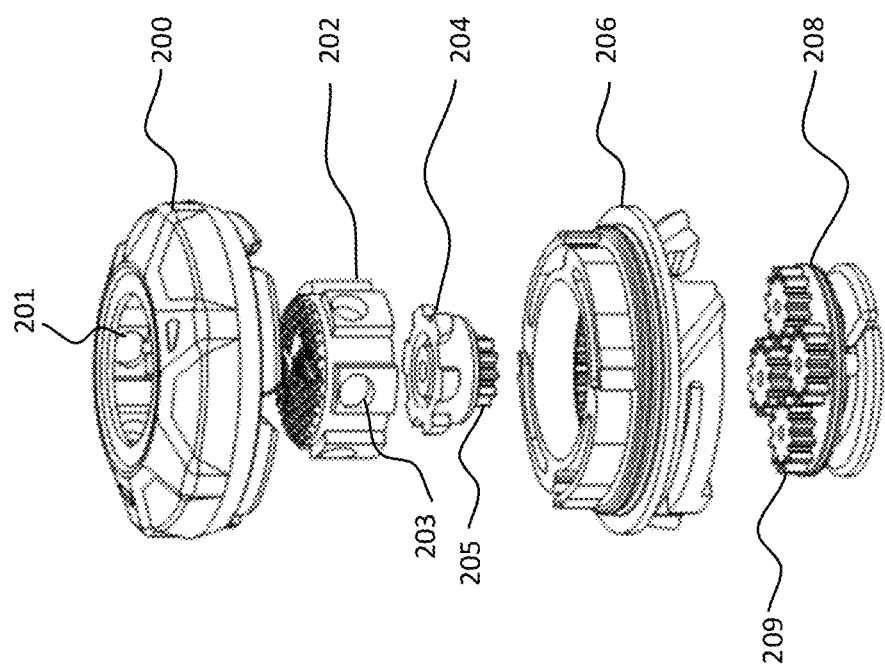
FIG. 20 depicts an embodiment of an adjustable tensioning device according to the invention described herein.

The clutch pieces of the previous example were held in the proper engaged position by means of a spring and the appropriate stops in the connected elements that limited the travel of the clutch pieces. An alternative or additional method to position the clutch pieces in a desired position is by the use of magnets. FIG. 20 is an illustration of the use of magnets to control the clutch positioning in a dial tensioning device.

The dial (200) has six interior spline slots that mate with the six splines on the exterior of the release button (202) which acts as the second clutch piece. The first clutch piece (204) is connected to the sun gear (205). The anchor ring (206), one embodiment of an anchoring element, comprises the flexible arms of the anti-unspooling mechanism (the mating recesses are located on the inner wall of the dial and are not visible in this view). The anchor ring also comprises the ring gear of the planetary gear system. The spool (208) acts as the carriage of the planetary gear system and supports the four identical planetary gears (209). There is a first set of six recesses (203) positioned in splines of the release button (202). These recesses are sized to hold a rare earth magnet. There is a second set of six more recesses (201) positioned in the slots in the dial into which the release button splines slide. The recesses (201) are also sized to hold a rare earth magnet or a suitable ferromagnetic element. The positions of the second set of recesses in the dial and the first set of recesses in the release button are situated such that the attraction of magnets in one set of recesses to magnets or ferromagnetic materials in the other set of recesses aligns the release button into the engaged clutch position.

Alternatively, magnets could be placed inside the release button (202) and inside the first clutch piece (204) and oriented to repulse each other to push the second clutch piece into the engaged position with the first clutch piece.

Example #6

A dial tensioning device with the components illustrated in FIG. 20 was 3D printed from nylon 12. Twelve 2×5 mm rare earth magnets were fit and glued into the first and second set of recesses as shown in FIG. 20. The magnets were oriented so that the magnets in the first set were attracted to magnets in the second set. The haptic feel of the release button when it was depressed to disengage the clutch was satisfying.

Anti-Unspooling Mechanism

In a preferred embodiment, the dial is turned clockwise to increase the tension element tension. Without an anti-unspooling mechanism, the spool would unwind the tension element once the user released the dial. The anti-unspooling mechanism should allow the user to turn the dial to increase the tension element tension but prevent unwinding even at high tension element tensions.

Pivoting pawls, flexible arms, dogs, cams, roller clutches, sprag clutches, and worm gears are all methods of providing one-direction rotation. Worm gears, cams, roller clutches, and sprag clutches can be nearly silent in operation and are preferred for situations which require noiseless operation (e.g., for the use in medical orthotics to be used in the field by the military). Flexible arms and dogs have the advantage of being simple mechanisms that function well in the presence of dirt and grit.

Figure 9B:
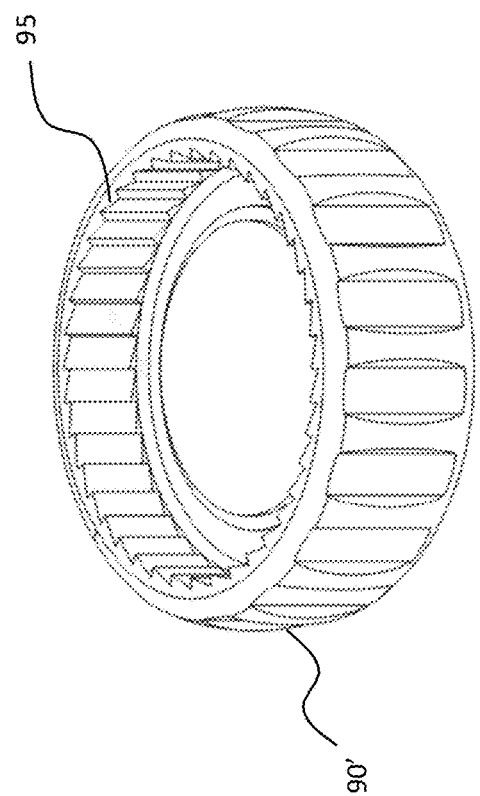
FIGS. 9a and 9b depict aspects of an embodiment of an adjustable tensioning device according to the invention described herein.
Figure 9A:
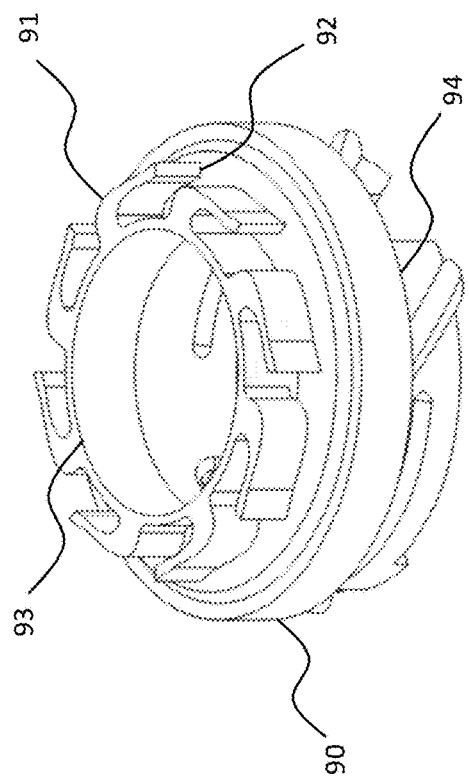

FIGS. 9*a* and 9*b* show examples of parts that comprise an anti-unspooling mechanism: a ring of flexible arms (90) and an array of corresponding recesses (90'). FIG. 9*a* shows the flexible arms integral with an anchor ring (94). There are eight identical flexible arms (91) of a generally curved shape. Each arm has a distal end (92) that is shaped to engage securely in one of the forty corresponding recesses (95) shown in FIG. 9*b*. The bases of the flexible arms (91) are connected to a ring (93) which is connected to the anchor ring (94). In FIG. 9*b* the array of recesses (95) are shown integral with a dial (in this example the dial and the array of recesses (90') are the same).

Figure 10:
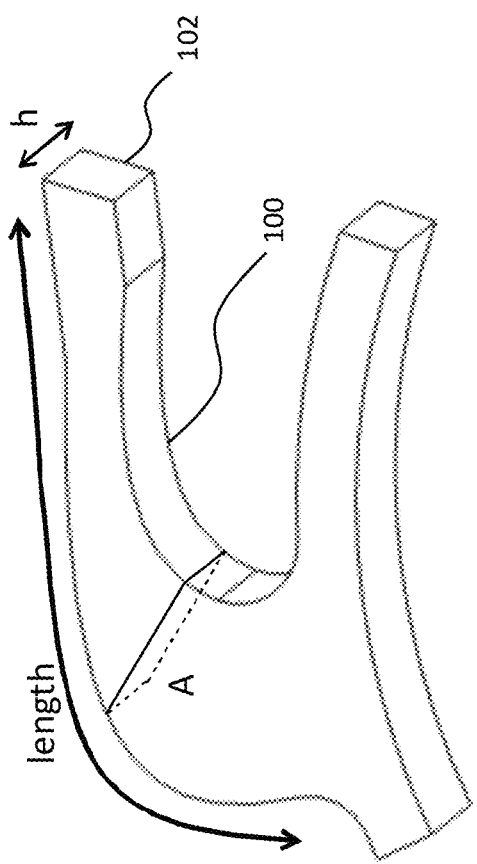
FIG. 10 depicts an aspect of an embodiment of an adjustable tensioning device according to the invention described herein.

FIG. 10 is an enlargement of a single flexible arm (100) shown in FIG. 9*a*.

Flexible arms have a height, h, and a length approximately described by the double headed arrow in FIG. 10. The cross-sectional area, A, may be uniform or may vary along the length of the flexible arm. The distal end or the tip of the flexible arm (102) mates with a corresponding recess or flat. The tip may be designed to fit into a single recess or flat, or multiple recesses or flats. The distal end of a pivoting pawl, flexible arm, or dog, can engage in a recess or flat of an opposing element. More than one pawl, flexible arm or dog can be employed to increase the resistance of the anti-unspooling mechanism to tension element tension. The pawls, arms, or dogs may be equally spaced radially or distributed in a pattern. In a preferred embodiment, all the distal ends of the pawls, arms, or dogs contact the opposing recesses or flats at the same time. That is, if there are 24 recesses or flats equally spaced circumferentially, it is preferred that there are 2, 3, 4, 6, 8, or 12 pawls, arms, or dogs equally spaced circumferentially so that the distal ends contact the recesses or flats at the same time.

The number of recesses and distribution of the pawls, arms, or dogs, can determine the amount the dial can unwind before the anti-unspooling mechanism catches and prevents unspooling. It is advantageous that the anti-unspooling mechanism prevents unspooling before, in an embodiment, at most 1/10th of unwind rotation occurs (that is, the anti-unspooling mechanism should prevent the dial from unwinding more than 36 degrees when the user releases the wind tension on the dial). Excessive unwinding makes it difficult for the user to apply the desired level of tension and is counter-intuitive which can lead the user to believe the anti-unspooling mechanism is not functioning properly. Increasing the number of recesses in the mating receiver will decrease the amount of unwinding before the anti-unspooling mechanism catches. However, increasing the number of recesses also decreases the maximum size of the recesses. This can be overcome somewhat by configuring the end of the pawl, flexible arm, or dog to engage multiple recesses at the same time. There is balance between the minimum number of recesses to prevent unacceptable unwinding and the maximum number of recesses before the recess geometry becomes ineffective at holding the pawl, flexible arm, or dog from unwinding.

A pawl, flexible arm, or dog can be modeled as a cantilevered beam. The compression strength of a pawl, flexible arm, or dog (that is, the ability to withstand the unspooling tension of the tension element) can be increased by selecting a material of higher young's modulus, the altering shape of the element (for example, to increase the cross-sectional area at one or more cross-sections along the element), and/or increasing the height of the element. All of these options will increase the bending resistance of a flexible arm, but increasing the height of the flexible arm increases it the least compared to the other two options. Thus, to retain ease of turning the dial in the tightening direction, it is preferred to increase the height of the flexible arm.

High flexing resistance can make the anti-unspooling mechanism difficult to turn in tightening direction and can result in a loud, unpleasant 'click' as the pawls, arm, or dogs flex into the recesses in the mating receiving ring. In addition, a high flexing resistance can cause undue wear of the pawl, flexible arm, or dog tip and/or the recess features leading to premature failure. In a preferred embodiment, it is desirable that the anti-unspooling mechanism turns quietly and easily in the tightening direction.

As mentioned herein, flexible arms and dogs can be employed in unspooling mechanisms because of their simplicity and resistance to fouling. Care must be taken to balance the stiffness of the cantilever beam of the flexible arms and dogs with the need to prevent unspooling under high tensions. As shown in FIGS. 9a and 9b, the flexible arms have distal ends (92) that fit into recesses (95). As the dial (90') is turned the distal ends (92) slide along the ramps of the recesses (95) until they drop into the notch or valley at the intersection an adjacent ramp. The sudden drop of the flexible arm or dog into the notch is what creates the clicking sound while winding the tensioning device. A deep notch and a high resistance to bending of the flexible arm or dog will make the anti-unspooling mechanism more secure yet will also tend to produce a louder clicking noise.

In embodiments, changing the saw-tooth pattern (a) shown in FIG. 28a of the recesses (95) into a sinusoidal pattern (b) allows the distal ends of the flexible arms or dogs to gradually descend into the notch or valley, thereby reducing or eliminating the clicking noise. However, a pure sinusoidal profile where the slope descending into the notch or valley (283') is the mirror of the slope of the ramp (281') could result in a less secure anti-unspooling mechanism. A blend of the two patterns (c) where the decent into the notch (283") is steeper than the ramp (281") leading up to it and/or where sharp transitions or corners are softened with a fillet can aid in reducing the clicking noise while minimizing the loss in security of the anti-unspooling mechanism.

Alternatively, the path of the distal end of the flexible arms or dogs can be modified such that the distal ends follow one path when traveling clockwise and on another path when traveling counter clockwise.

FIG. 28b shows a top down view of one such embodiment. A path is defined by a groove (285) that runs continuously around the figure. The depth of the groove defined by (285) is uniform although in other embodiments the depth could vary locally and gradually. A distal end of a flexible arm or dog (not shown) rides inside the groove, in aspects. In aspects, when the flexible arm or dog is turned in a clockwise direction, the distal tip moves continuously around the path (285). Since the depth of the groove can be uniform (or gradually changing) there is no abrupt change that creates a clicking noise while the distal end rides in the groove.

A branch (286) can be placed along the path (285) periodically. The branch (286) can be roughly the same depth as the path (285) where they meet but then ramp when the paths diverge. In aspects, when the flexible arm or dog is traveling counterclockwise along the path (285), the distal end is trapped in the branch (286) and thereby creates the anti-unspooling mechanism.

In embodiments, the cantilever beam defined by the flexible arm or dog can have two different bending forces: a bending force in the outward radial direction and a stronger bending force in the downward (into the paper) direction as shown in FIG. 28b. As the flexible arm or dog move clockwise around the path (285) the radial bending force can cause the distal end to contact the outer wall of the groove or path. This can be a continuous path with no abrupt changes and therefore no clicking noise is created. A second, stronger bending force can push the distal end of the flexible arm or dog into the bottom of the groove. In aspects, there is no abrupt change in the depth of the groove (285) so no clicking noise is generated, or a lower sound is generated (e.g., substantially no clicking noise, or a lower clicking noise than without the design described above).

In aspects, when the distal end of the flexible arm or dog travels in the counterclockwise direction, the stronger bending force pushing the distal end into the bottom of the groove forces the distal end into the branch (286), which can have a deeper bottom than the groove (285).

Example #7

Two flexible arm anti-unspooling mechanisms were 3D printed from nylon 12. The design of the arms was similar as shown in Figures A and B. The first example had 4 arms; the second had 6 arms. The corresponding opposing element had 24 recesses 1.5 mm deep. The arms were 5 mm in height. Both anti-unspooling mechanisms turned easily in the clockwise direction. The 4 armed element failed when subjected to a 200 lbs. tension element tension on the spool, whereas the 6 armed element was able to withstand a 200 lbs. tension element tension.

Example #8

15 wedge shaped dogs 2 mm in width and 1.5 mm in height were designed into the inside surface of a dial which was 3D printed out of nylon 12. The opposing elements were an equal number of reciprocal wedges in the piece upon which the dial rotated. As the dial was turned, the dogs bumped up over the top of the opposing wedges. When seated into the opposing wedges, the dial prevented a spool from unspooling under a tension of approximately 75 lbs.

Changing the length of the pawl, flexible arm, or dog, can also affect the bending resistance of the element. A longer pawl, flexible arm, or dog will be less stiff and less resistant to bending. In theory, the compressive strength of a beam is independent of the length of the beam. In practice, a beam will buckle before its compressive strength is exceeded and since the force that causes buckling decreases as the beam length increases, increasing the pawl, flexible arm, or dog length to decrease the bending resistance can result in a reduction in anti-unspooling strength. Buckling failure of the pawls, arms, or dogs can be reduced by providing side support to the pawl, flexible arm, or dog. In particular, if the pawl, flexible arm, or dog is designed with an inherent curve the direction of buckling can be determined and support to the outer side of the pawl, flexible arm, or dog can be provided.

Example #9

An anti-unspooling mechanism was 3D printed from nylon 12 consisting of 4 curved arms 15 mm long, 5 mm tall and approximately 5 mm2 in cross section. The end of the arms were configured to engage with two notches in the recesses of the mating ring. Forty recesses 1 mm deep were equally spaced along the interior wall of the mating ring. The anti-unspooling mechanism allowed easy turning in the tightening direction but withstood >120 in-lbs of torque in the loosening direction. As unwinding force increased, the arms flexed outwards and were supported by the mating ring to prevent premature buckling.

Figure 11:
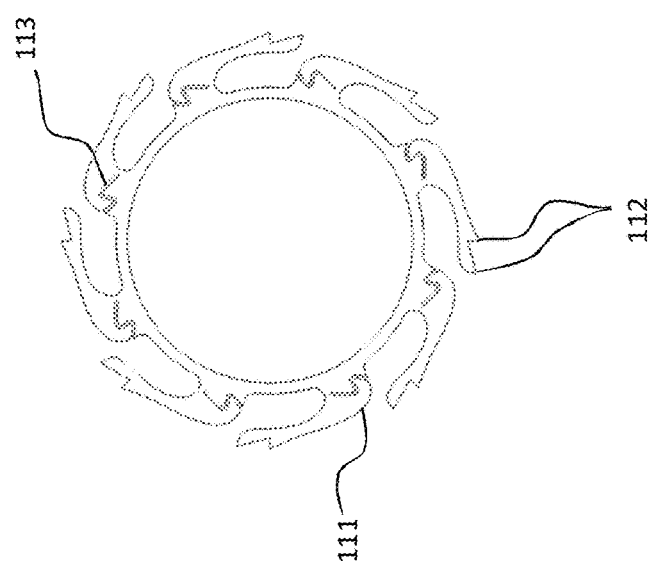
FIG. 11 depicts an aspect of an embodiment of an adjustable tensioning device according to the invention described herein.

A relief can be cut into the pawl, flexible arm, or dog to act as a hinge and decrease the bending resistance. The hinge preferentially bends in one direction but resists bending in the opposite direction. In this manner, the pawl, flexible arm, or dog can have a low bending resistance but a high anti-unspooling resistance. FIG. 11 shows another example of flexible arm design (111). In this example, each distal tip (112) of the flexible arms are configured to fit into two adjacent recesses in the corresponding mating element. A curvilinear relief (113) is provided which extends through the height of the flexible arm. The relief is designed such that the tip of the flexible arm can bend readily inwards toward the center but it is difficult for the tip to bend outwards away from center. In this manner, the flexible arm can pivot out of the way when the dial (with the corresponding recesses) is rotated in the clockwise direction. When the dial (and corresponding recesses) is rotated in the counterclockwise direction the arm will resist the rotation thereby providing an anti-unspooling function.

Figure 12:
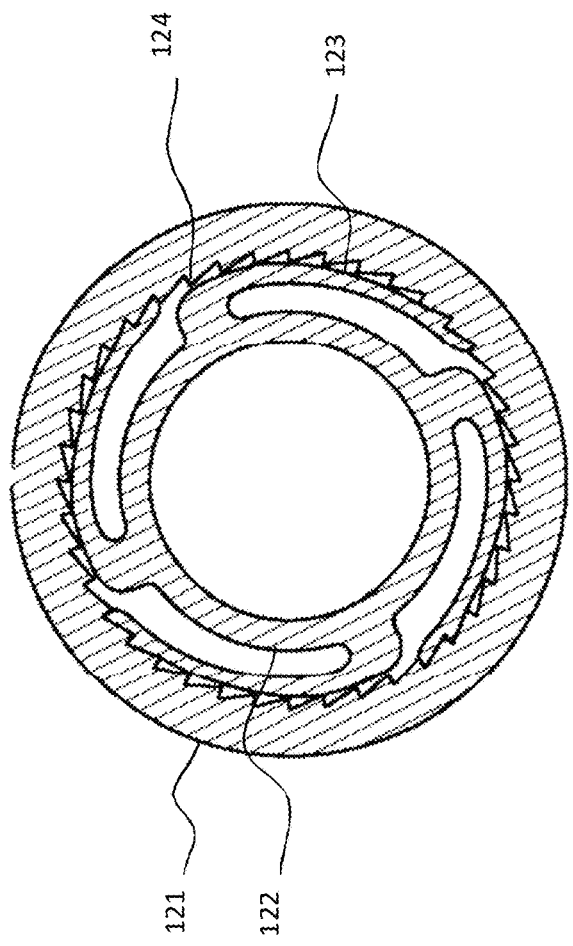
FIG. 12 depicts an aspect of an embodiment of an adjustable tensioning device according to the invention described herein.

FIG. 12 shows a cross sectional view of yet another example of a flexible arm configuration. Element 121 (the array of recesses) and element 122 (the array of flexible arms) work together to provide an anti-unspooling feature. The arm lengths (123) in FIG. 12 are nearly twice as long as the flexible arms (111) depicted in FIG. 11. The large aspect ratio (length to cross sectional area) of the flexible arms in FIG. 12 would be subject to buckling at lower forces than the flexible arms in FIG. 11. The outward curvature of the flexible arms (123) in FIG. 12 determines the direction of buckling. In the example shown in FIG. 12, the arms would buckle away from the center of the element 122. The peaks of the recesses (124) end up supporting the arms and hinder the buckling.

Example #10

An anti-unspooling mechanism was 3D printed from nylon 12. Eight arms were arranged uniformly, circumferentially around the outer perimeter of the anti-unspooling mechanism. Each arm was 5 mm tall and approximately 12 mm long. A zig-zig recess was cut along the base of each arm. The anti-unspooling mechanism turned easily in the tightening direction and held firmly in the unwinding direction and withstood 180 in-lbs of unwinding torque.

A second device was hooked to a motor and rotated more than 5,000 times to simulate wear. The force required to unwind the anti-unspooling mechanism was measured to be 140 in-lbs of torque. The low bending resistance reduced the wear of the arm/recess features while still providing a high unspooling resistance.

Figure 21:
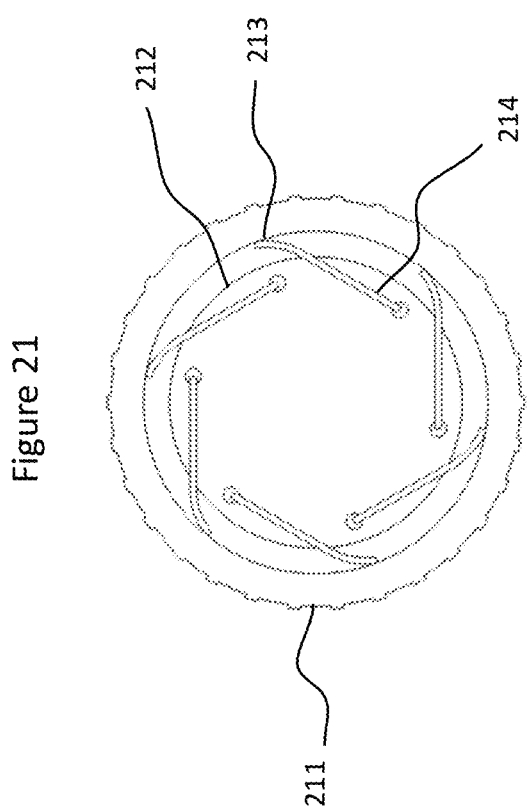
FIG. 21 depicts an embodiment of an adjustable tensioning device according to the invention described herein.

In another embodiment, the flexible arms or vanes can be made of metal such as spring steel. Recesses can still be utilized to provide an audible 'click' and to provide a detent that defines the increment of tensioning that the dial can provide before unwinding slightly before the pawl, flexible arm, or dog engages the recess. However, if the mating element is considerably softer than the material of the flexible arm, the flexible arm can stick into the surface of the mating element slightly (in effect, creating a recess 'on the spot'). An anti-unspooling mechanism made in such a manner could operate silently (without the 'clicking' noise from the pawls, arms, or dog settling into a corresponding recess) and would minimize the amount of unwinding allowed when turning the dial. FIG. 21 is a top view of anti-unspooling mechanism made with spring steel vanes as the flexible arms. An inner circle (212) has six identical slots arranged around the circumference of the piece. Six pieces of spring steel (214) are inserted into the slots to act as vanes or flexible arms. The distal tips (213) of the vanes rub on the inner wall of an outer dial (211). When the dial is rotated clockwise in relation to the inner circle, the vanes drag against the inner wall. When the dial is rotated counterclockwise in relation to the inner circle, the tips of the vanes (213) dig into the inner wall and prevent such rotation.

Example #11

An anti-unspooling mechanism was made by 3D printing a spool/carriage from nylon 12. Six slots roughly 1 mm wide and 10 mm long were designed into the carriage. A portion of 0.008" thick spring steel was cut into 3 mm tall by 12 mm long rectangles. The rectangles were glued into three of the six slots (leaving the other three slots empty). A dial with forty V-shaped recesses designed into the inner wall was placed over the spool/carriage. The dial could be turned easily in the winding direction but resisted an unwinding tension of more than 100 lbs on the spool. The anti-unspooling mechanism can be built into the second piece of the clutch, the torque multiplier system, or the dial element. Incorporating the anti-spooling element in proximity to the spool reduces the forces that could pitch, tilt, cant, or move the spool out of position. Alternatively, affixing the anti-spooling element to the dial or the input side of the torque multiplier system reduces the amount of force on the, for example, flexible arms of the anti-unspooling mechanism. The, for example, flexible arms can be made with a smaller cross-section or shorter, which allows them to turn more easily in the tensioning direction while securely preventing the spool from unwinding under high tension.

Torque Multiplier System

The high tensions required for a medical orthotic or prosthetic (e.g., in aspects, >200 lbs.) can create a need for a torque multiplier system of the adjustable tensioning device. A torque multiplier system can be made designing the diameter of the dial to be larger than the diameter of the spool. However, there is a practical and aesthetic limit to how large the selected diameter of the dial can be, and a functional limit to how small the diameter of the spool can be made before tension element cutting becomes a failure mechanism. Thus there is a need for a torque multiplier system that can be used in addition to the offset in the dial and spool diameter.

Examples of torque multiplier systems suitable for a medical orthotic adjustable tensioning device are planetary gear drives, cycloidal gear drives, gear trains, and worm screw/worm gear combinations, and the like, and combinations thereof. Another method to multiply the force is to select an appropriate path of the tension element itself through pulleys, rings, guides, and the like, to generate a mechanical advantage (e.g., a block and tackle or the equivalent). In aspects, combinations of torque multiplication elements such as gear trains, dial/spool diameter combinations, and tension element path can be used in conjunction.

Figure 13:
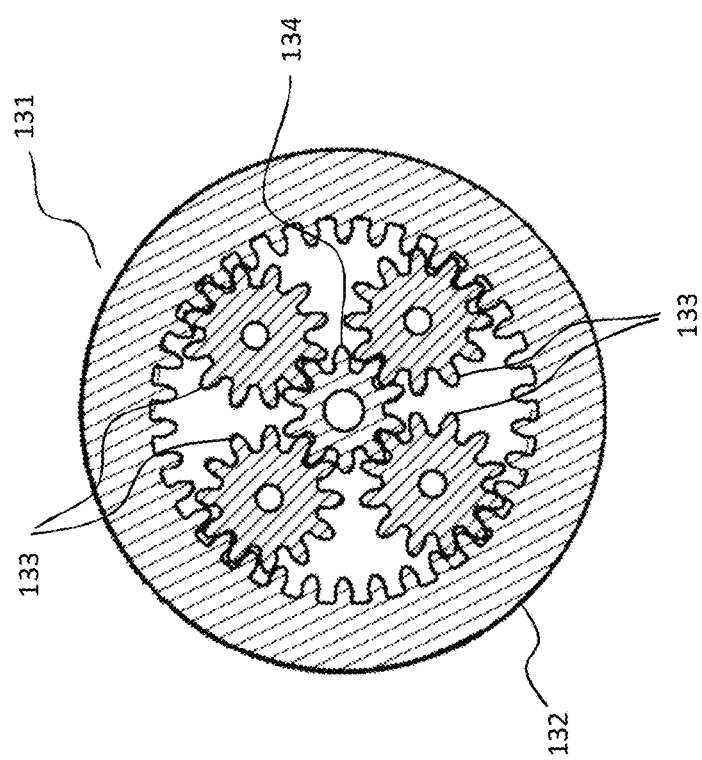
FIG. 13 depicts an aspect of an embodiment of an adjustable tensioning device according to the invention described herein.

Planetary gear drives are made of a sun gear, several planetary gears, and a ring gear (sometimes called an 'internal gear'). A cross-sectional view of an example of a planetary gear drive (131) is shown in FIG. 13. Traditionally, the planetary gears (133) are mounted in an element called a carriage (not shown). If the ring gear (132) is fixed (kept from turning), rotating the sun gear (134) will cause the carriage to turn. The ratio of rotation of the sun gear versus the rotation of the carriage is 1 plus the number of teeth in the internal gear divided by the number of teeth in the sun gear.

For example, for module 1.0 gears, if the sun gear has 10 teeth, its pitch diameter will be around 10 mm. If the planetary gears also have 10 teeth, their pitch diameter will also be around 10 mm. The pitch diameter of the ring gear will be 2*10 mm+10 mm, or 30 mm. The ring gear will therefore have 30 teeth. The ratio of rotation of the sun gear to the carriage will be 4:1. Using the planetary gear drive described, applying a torque of 25 lbs. to the dial will result in a torque of 100 lbs. to the spool (assuming, for the sake of this example, that the diameter of the dial and spool are the same.)

In aspects, the minimum size of a planetary gear drive is determined by the diameter of the ring gear. To decrease the size of the planetary gear drive one can reduce the number of teeth in the sun and planetary gears and/or reduce the gear module. There is a practical limit on the minimum number of teeth in a gear; it can lie between 7 and 16 teeth, in examples. The minimum size for the module of the gear (making the size of the teeth smaller) depends on the load applied and the material of which the gear is made. The resolution of current commercial multi jet fusion 3D printers sets a practical limit of about 0.5 module gears.

Increasing the thickness of a spur gear is an effective way of increasing the amount of load it can handle. Helical gears are also stronger than spur gears and have the advantage of gradually contacting the opposing tooth faces rather than the all-or-nothing contact of a traditional spur gear. Helical gears create a radial force when engaged which can be detrimental. Herringbone gears have a net zero radial force but are difficult to manufacture using traditional manufacturing methods.

Example #12

A planetary gear drive was made using a 5 mm tall module and 1.2 gears. The sun gear had 10 teeth. The four planetary gears had 12 teeth. The ring gear had 34 teeth. The gears were 3D printed from nylon 12. The sun gear was fabricated into a dial and the carriage holding the planetary gears was connected to a spool. By turning the dial, it was possible to apply a 200 lbs. tension to the tension element wrapped around the spool without any of the gear teeth in the sun gear, planetary gear, or ring gear from failing.

Planetary gear drives can be stacked. Affixing a sun gear to one carriage can drive a second carriage. In this manner the effective gear ratio of the first carriage is multiplied by the effective gear ratio of the second carriage. If the correct combinations of sun/planetary gear sizes are selected, the first and second carriage can use a common ring gear.

Figure 14:
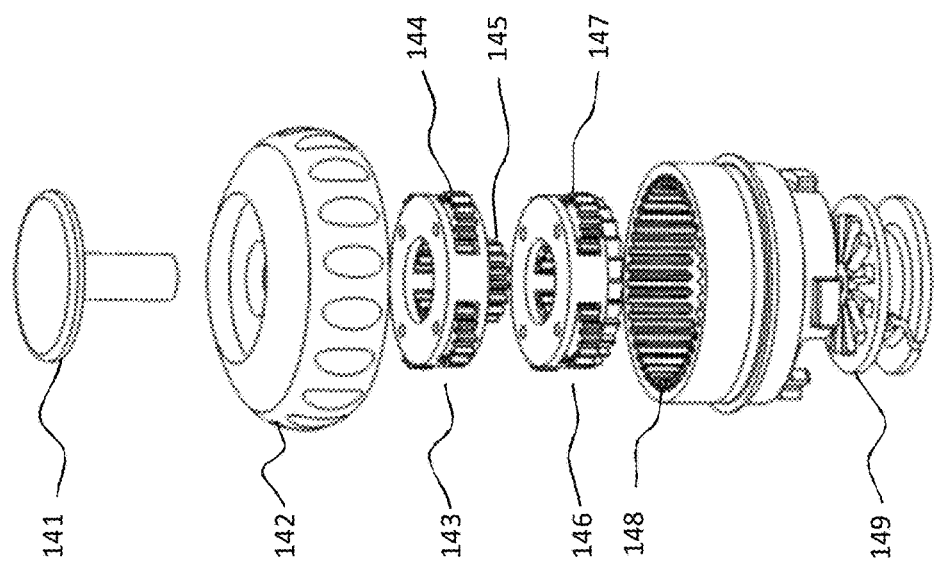
FIG. 14 depicts an embodiment of an adjustable tensioning device according to the invention described herein.

FIG. 14 shows an exploded view example of a double stacked planetary gear drive. The release button (141) is centered in the dial (142). Disposed on the interior of the dial is a sun gear (not shown) that engages with the upper carriage (143). Four identical planetary gears (144) are driven by the sun gear in the dial (142). The planetary gears (144) engage in the teeth of the ring gear (148). When the dial is turned, the sun gear drives the upper carriage with a mechanical advantage, $MA_1$, equal to the number of the teeth in the ring gear ($T_R$) divided by the number of teeth in the first sun gear ($T_{FS}$) plus one. A second sun gear (145) is connected to and driven by the upper carriage (143). The second sun gear (145) in turn drives the four identical planetary gears (147) of the lower carriage (146). The lower carriage planetary gears (147) also engage the teeth of the ring gear (148). The mechanical advantage, $MA_2$, of the lower planetary gear drive is the number of teeth in the ring gear ($T_R$) divided by the number of the teeth in the second sun gear (Tss) (145) plus one. There is an additional mechanical advantage, $MA_3$, derived from the ratio of the diameter of the dial (142) with the diameter of the spool (149). The combined mechanical advantage of the dial tensioning system shown in FIG. 14 is: $MA_1 \times MA_2 \times MA_3$.

Figure 15:
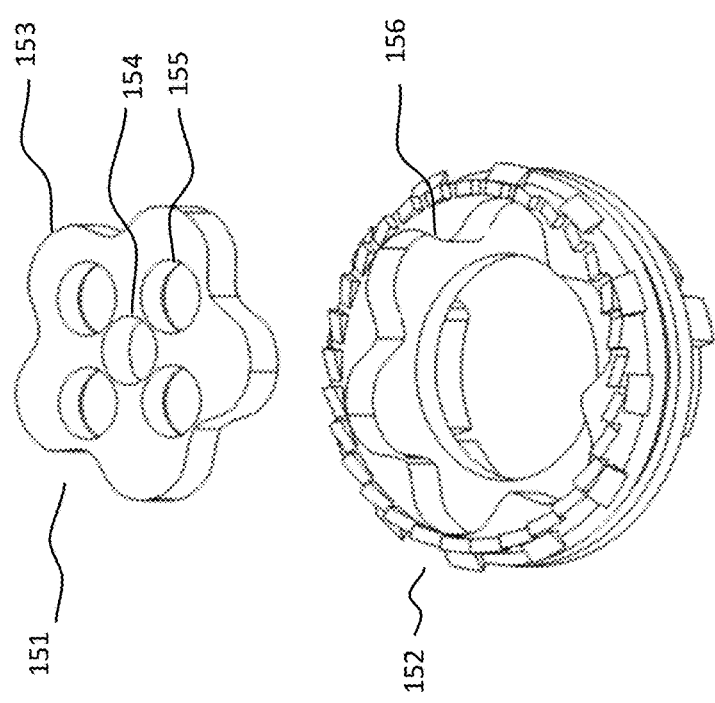
FIG. 15 depicts an embodiment of an adjustable tensioning device according to the invention described herein.

Cycloidal gear drives can provide high gear ratios (torque multiplier) in a compact form, such as gear ratios from 10:1 to 300:1. FIG. 15 is an example of a 6:1 torque multiplier cycloidal drive. A cycloidal gear (151) rides inside a housing (152). There are five identical lobes (153) on the gear and six corresponding recesses (156) in the housing. An off-centered drive pin (not shown) engages the cycloidal gear center hole (154). When the cycloidal gear is rotated by the drive pin one lobe is forced into a recess. Because there is one fewer lobe than there are recesses, the cycloidal gear completes one revolution for every six revolutions of the off-centered drive pin. The output of the cycloid gear can be coupled to another element (not shown) by means of eccentric pins (not shown) that ride in the holes (155).

Example #13

A cycloidal gear drive torque multiplier system was made with a disc of 2 mm thickness and 5 lobes. The ring had 5+1 lobe for a torque multiplication factor of 6:1. An eccentric cam (with an eccentricity of 2 mm) was driven by a dial. Under even moderate tension element tensions, the cam popped out of the disc, in experiments.

Worm screw/worm gear drives can be used where a high torque multiplier is needed. Worm screw/worm gear drives also have the advantage that they cannot be backdriven. That is, a torque applied to the worm gear (the output) does not cause the worm screw (the input) to turn. A worm gear/worm screw system can remove the need for the anti-unspooling mechanism. It can also allow the user to reduce some tension on the tensioning device by unwinding the worm screw without the need to completely release all the tension.

Figure 16:
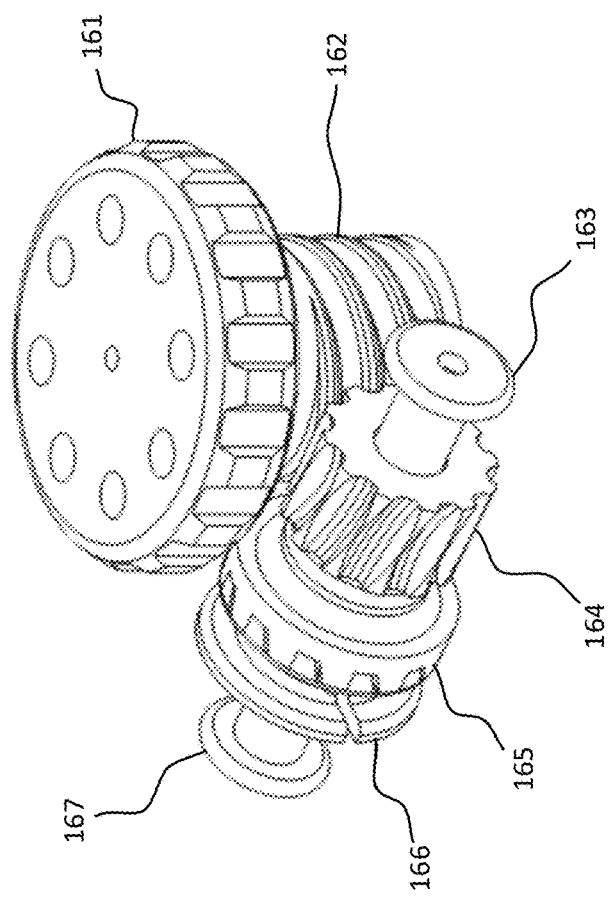
FIG. 16 depicts an embodiment of an adjustable tensioning device according to the invention described herein.

FIG. 16 is an illustration of a 6:1 mechanical advantage worm drive. A dial (161) is connected to a worm screw (162). The worm screw as shown has two thread starts. That is, there are two threads that wrap around the worm screw in a helix offset from each other. The threads of the worm screw engage with the cuts in the worm gear (164). There are twelve cuts along the circumference of the worm gear (6:1 mechanical advantage times 2 starts=12 cuts). The advantage of using multiple starts on the worm screw is that more than one thread can be engaged with the worm gear at any given time which improves the ability to transmit high torques from the worm screw to the worm gear. The worm gear is connected to a spool (166) via a clutch element (165). The release button (163) rides in a hollow shaft through the worm gear and the clutch element. Pushing on the release button moves the spool (166) to the left as shown in FIG. 16, which allows the spool to spin freely. Pushing on the engage button (167) re-seats the spool in the clutch element binding its rotation to the worm gear. Since worm screws cannot be backdriven by torque on the worm gear, there is no need, in embodiments, for a further anti-unspooling mechanism; in other words.

Example #14

A worm screw/worm drive system was generated with a worm screw 25 mm in diameter and a thread pitch of 10 mm. The thread had two starts (that is, there were two independent threads wrapped around the shaft). A worm gear 12 mm width and 19 mm in diameter was positioned with its axis of rotation at 90 degrees to that of the worm screw's axis of rotation. The mechanical advantage of the worm screw/worm gear combination was 6:1. Turning the worm screw 6 times causes the worm gear to rotate once. When the worm screw was turned, the threads of the worm screw jumped the corresponding threads in the worm gear at tension element forces above 30 lbs.

Traditional gear trains offer a wide variety of design choices for a torque multiplier system but they may not be as compact as planetary or cycloidal gear trains. They are, however, often simpler to design, manufacture, and assemble than planetary or cycloidal gear trains. Almost any gear ratio desired can be designed using traditional gear trains.

Figure 17:
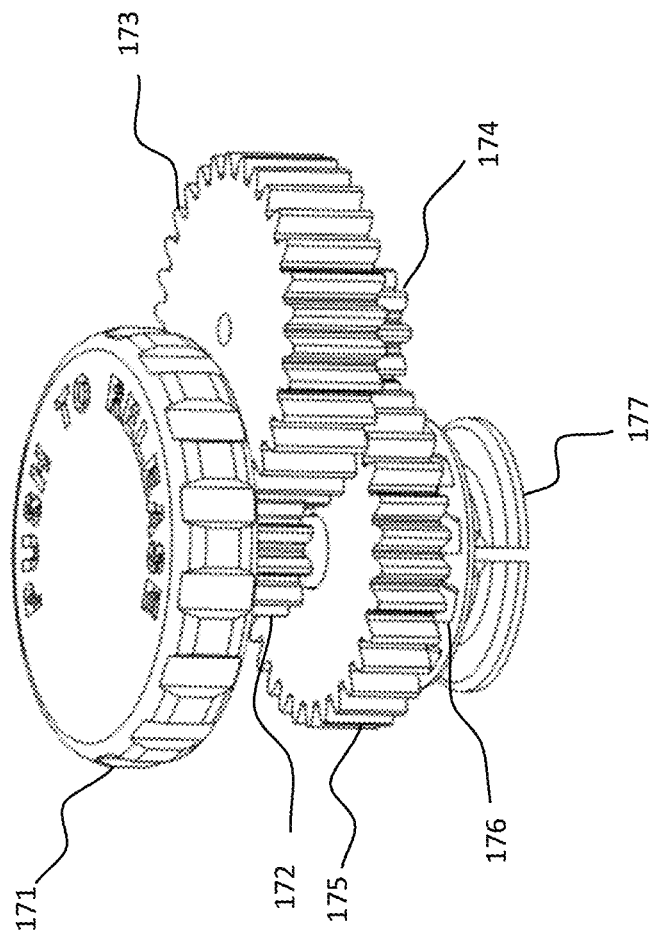
FIG. 17 depicts an embodiment of an adjustable tensioning device according to the invention described herein.

FIG. 17 is an illustration of an example of a typical gear train suitable for use in a dial tensioning device. A dial (171) is connected to a small diameter drive gear (172). The drive gear couples with a larger diameter driven gear (173). The mechanical advantage of these first two gears, $MA_1$, is determined by dividing the number of teeth $(T_2)$ in the driven gear by the number of teeth in the drive gear $(T_1)$: $MA_1=T_2/T_1$. A second small diameter drive gear with a number of teeth, $T_3$, (174) is coupled with the driven gear (173). This second drive gear is coupled with a second large diameter driven gear (175) which has a number of teeth $T_4$. The mechanical advantage from these two gears is: $MA_2=T_3/T_4$. The drive shaft of the dial/first drive gear passes through a hole in the second driven gear. The face width of the first driven gear is larger than the face width of the first drive gear which enables the dial/first drive gear ensemble to slide along the first driven gear without disengaging. Pushing on the dial/first driven gear/shaft presses on the face on one of the clutch elements (176) to disengage the spool (177). A spring (not shown) returns the spool to the engaged position when the force pushing the dial down is released. Since ordinary gear trains can be back-driven, an anti-unspooling mechanism(s) would, in embodiments, need to be employed to prevent the spool from unwinding prematurely. The total mechanical advantage of the system shown in FIG. 17 is the ratio of the dial diameter $(D_{dial})$ with the spool shaft diameter $(D_{shaft})$ times $MA_1$ times $MA_2$.

Example #15

In embodiments, a pulley system is used wherein pulleys generate a mechanical advantage. Using this system, one can increment or decrement tension by rotating the dial one way, and loosing by rotating the dial in a second direction. This pulley system can use at least one fixed pulley or anchor point and at least one free or moveable pulley or anchor point, wherein the position of the free pulley will move as the tensioning element is wound and unwound. With this system, the mechanical advantage can be changed using different arrangements of the anchor points as well as adjustments of the pulley path. The pulley system can act in-between the tensioning line and the rotatable (tension) dial giving the user a mechanical advantage when they increase or decrease tension.

Figure 18:
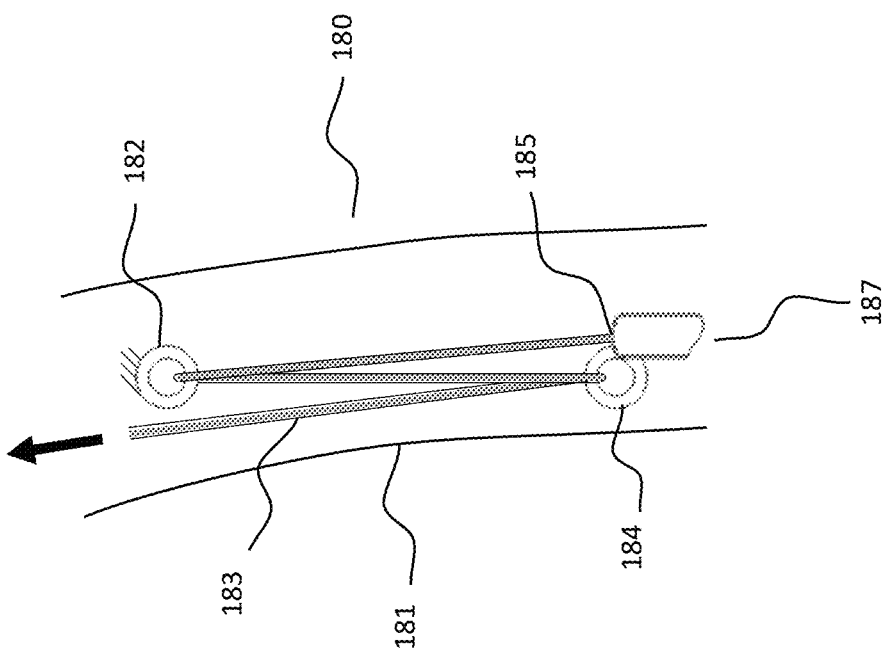
FIG. 18 depicts an embodiment of an adjustable tensioning device according to the invention described herein.

FIG. 18 is an example of a pulley system (180) derived to provide a mechanical advantage for a tensioning system. A frame element (181) is shown in outline. One end of a tension element (183) is anchored at a position (185) to an internal component (187) of the frame element (for example, an energy storage element of an orthotic). The tension element is looped through a ring (182) (or pulley, or the like) that is anchored to the frame element. The tension element then loops around a second ring (184) (or pulley or the like) that is affixed to the same component (187) where the anchor position (185) terminates. The tension element then continues along the direction shown by the arrow in FIG. 18. The tension element may be connected to a dial tensioning element, a lever, another pulley system or the like. Pulling on the upper end of the tension element imparts a 2:1 mechanical advantage to the tension imparted on the internal component (187). In other exemplary embodiments where the torque multiplier element is a pulley system, the pulley system may be a fixed, movable, compound, or block and tackle pulley system. The system may comprise one or more pulleys to yield mechanical advantages ranging from 2:1 to 20:1 or greater.

Example #16

A knee orthotic was fabricated using 3D printing from nylon 12. A tensioning dial with a 3:1 mechanical advantage was used. An energy storage element was situated across the hinge elements on both the medial and lateral sides of the orthotic. One of the distal ends of the energy storage element was anchored to the lower frame. The other distal end of the energy storage element was connected to tensioning dial with a substantially inelastic cable 1.2 mm in diameter made of UHMWPE. The path of the cable is shown schematically in FIG. 18. Polished steel oblong rings were used as the "pulleys" for the cable to slide upon. The torque multiplier of the cable-pulley system was 2:1. The total torque multiplier of the orthotic was 2:1 of the cable path times 3:1 of the dial for a result of 6:1. The cable-pulley system was then routed in such a way to create at 3:1 torque multiplier, and coupled with a 3:1 dial to spool ratio, resulting in a total mechanical advantage of 9, showing, through experimentation, that the system and device according to the current invention can be engineered to achieve higher force multipliers by adjusting the dial to spool ratio and cable-pulley mechanical advantage.

A dial tensioning device needs a method to release the tension on the tension element. Dial tensioning devices suitable for apparel and sports such as those made by BOA Technologies, YOW Systems, FidLock, and FitGo Technologies most often use a 'pull to release' mechanism. When the user pulls up on the dial, the spool is allowed to turn freely which releases the tension on the tension element. A 'push to release' mechanism can also be used to release the tension on a dial tensioning device as shown in FIGS. 1, 14, 16, 17, and 20.

The 'push to release' mechanism can be configured to release only while the user is actively pushing the release button. This configuration is a single stable state system: engaged. (In other words, when the user isn't actively pushing on the release button, the device is engaged by default.) Alternatively, a release mechanism can be configured to have two stable states: engaged or disengaged. An example of a device with two stable states is a ball point pen. Clicking on the cap extends the pen for writing where it remains until the cap is clicked again wherein the pen retracts. This is known in the art as a "push-push latch".

Figure 22:
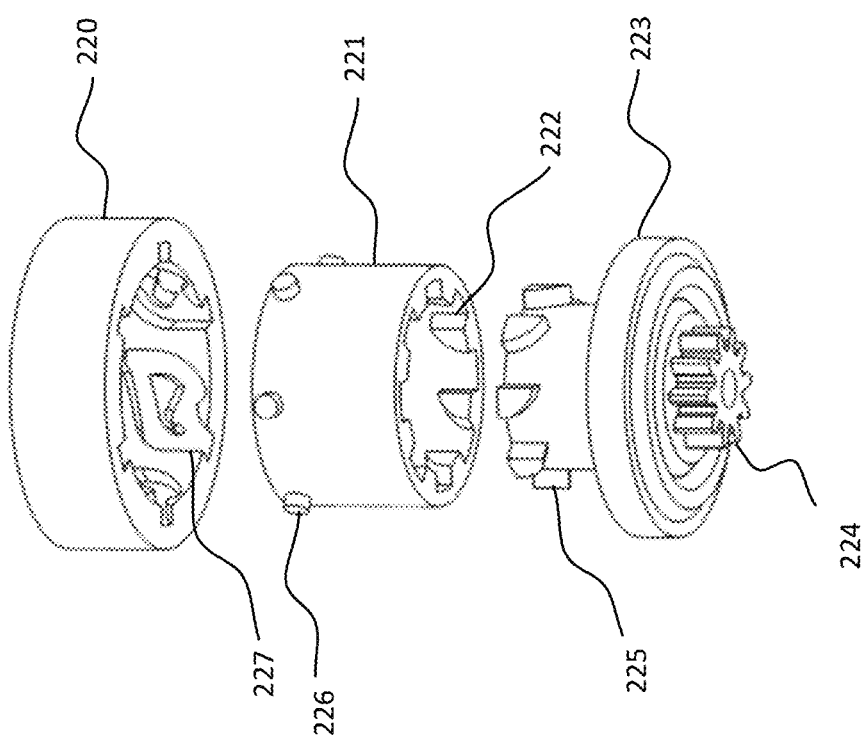
FIG. 22 depicts an embodiment of an adjustable tensioning device according to the invention described herein.

FIG. 22 is an illustration of one embodiment of a bi-stable release button. A release button (221) fits into a sleeve (220). The release button serves as the second clutch piece and has eight clutch features (222) arranged on its lower, inner surface. A first clutch piece (223) is integral with a sun gear (224) of a planetary gear system. The first clutch piece has eight clutch features (225) arranged along its upper, outer surface. Stable state 'engaged' occurs when the clutch features (222) and (225) are touching each other. This happens when the release button is at a specific height. Stable stage 'disengaged' occurs when the clutch features (222) are lower than the clutch features (225). This happens when the release button is a second, different height (lower than the first). Six bosses (226) are arranged around the upper, outer surface of the release button. The bosses ride in race track grooves (227) cut into the inner surface of the sleeve. A spring (not shown) between the first clutch piece and the second clutch piece pushes the release button upwards. The race track (227) is designed so that the two stable locations of the bosses (226) correspond to the engaged and disengaged heights of the clutch features.

Figure 27:
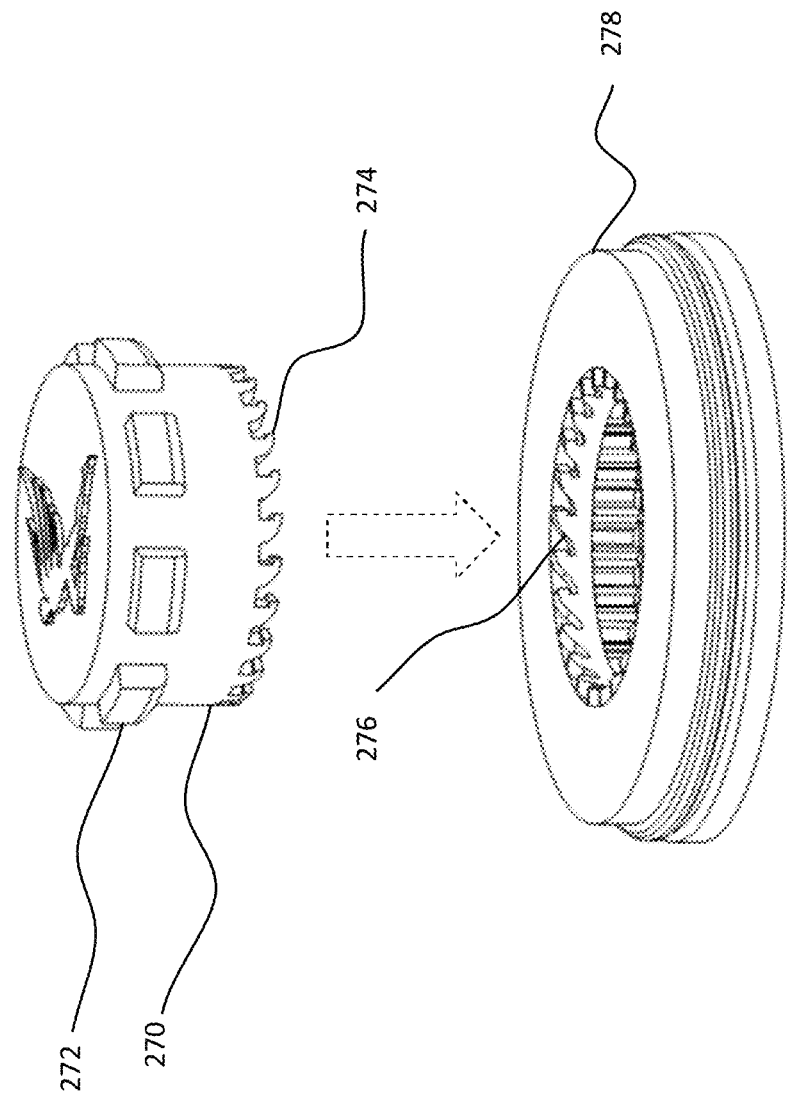
FIG. 27 depicts an embodiment of an adjustable tensioning device according to the invention described herein.

Another type of bi-stable release button suitable for a dial tensioning system is shown in FIG. 27. FIG. 27 shows an embodiment of a "push-turn latch". The button (270) and the receiving element—in this case the anchor ring (278)—are shown in an exploded view. The button (270) is able to move axially within the dial (not shown for clarity). Eight identical splines (272) are located circumferentially around the outside of the button. The splines allow the button to slide axially up and down in corresponding grooves in the dial (not shown) but prevent the button from rotating freely within the dial. In this manner, torque applied to the dial is transmitted to the release button (which is in turn an element of the clutch as described in the configuration shown in FIG. 22). The release button has teeth (274) arranged along the bottom edge. These teeth mate with recesses (276) in the receiving element (278). When the release button is pressed downwards to disengage the clutch as shown by the dashed arrow in FIG. 27, the lower edge of the button teeth forces the button to turn (slightly) counter-clockwise when it contacts the receiving element. The tabs at the distal ends of the teeth (274) engage in the recesses (276) and prevent the button from popping up when the user stops pushing the button down. When the user turns the dial clockwise to tighten it, the button also rotates clockwise. The button teeth disengage from the recesses allowing it to pop back up into the clutch engaged position. In aspects, a dial tensioning device incorporating some or all of the elements described above can be configured as a modular component that is a fully (or nearly fully) assembled, independent device that is meant to be attached to another article to be used. In embodiments, such a modular component is fully functional by itself and ready for use after being mounted and configured appropriately. For example, in aspects, a dial tensioning device that was configured as a modular component would be ready to use after being mounted on another article (e.g., an orthotic device) and the tensioning elements affixed to the spool.

Modular components are often manufactured by one party and sold to a second party who subsequently incorporates the modular component into their product. This is the basis of Industry 2.0 where piecework and assembly lines were commonly adopted. In this paradigm, element and part designs (that is, the subcomponents of the modular components) are optimized for the manufacture of the modular component, not necessarily for the finished assembly for which the modular component is intended. Industry 3.0 and 4.0 (Digitization and Network) are changing this paradigm with the adoption of 3D printing which enables embedded functionality.

Figure 23:
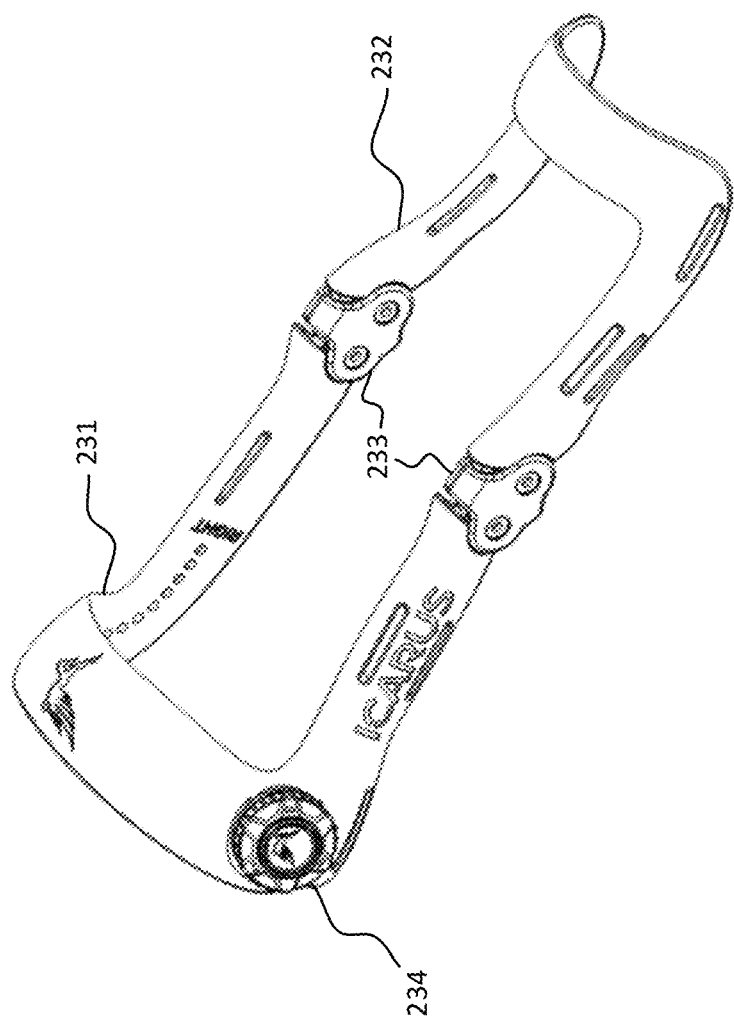
FIG. 23 depicts a medical device (e.g., orthotic) including an embodiment of an adjustable tensioning device according to the invention described herein.

FIG. 23 is a perspective view of a dial tensioning device embedded in a double upright dynamically unloading knee brace. The knee brace is comprised of an upper frame (231), a lower frame (232), and hinge connection elements (233). The dial tensioning device (234) is embedded directly into the upper frame. The upper frame contributes critical functionality to the dial tensioning device (described below). In a similar manner, the dial tensioning device contributes critical functionality to the dynamically unloading knee brace orthotic. The distinction between the orthotic and the dial tension mechanism blurs in the embodiment shown in FIG. 23.

Figure 24:
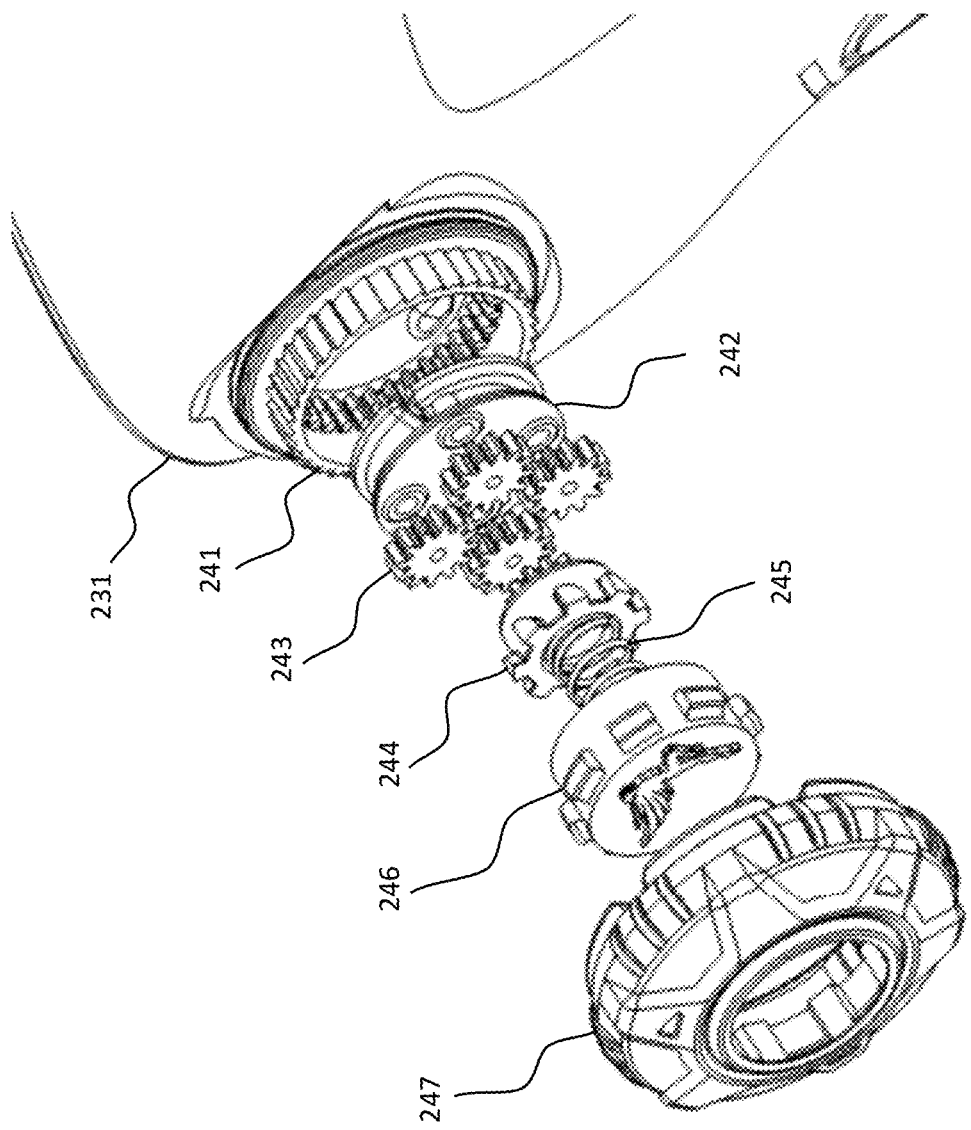
FIG. 24 depicts an embodiment of an adjustable tensioning device according to the invention described herein.

An exploded view of the embedded dial tensioning device in a portion of a top frame (231) is shown in FIG. 24. As in FIG. 20 (which is an example of a modular component dial tensioning device) there are the functional equivalents of a dial (247), an anti-unspooling mechanism, a clutch/release element (246, 245, and 244), a spool (242), a torque multiplier, and a socket (241). The anti-unspooling mechanism comprises flexible arms (not readily visible under the dial) and the mating recesses on the socket (241). The clutch element comprises a release button (246) with second clutch pieces arranged internal to the button cylinder. A spring (245) maintains the restorative force to keep the button in the upper, engaged position. The sun gear drive (244) has first clutch pieces arranged externally around the sun gear drive cylinder. The torque multiplier system comprises the planetary gear drive comprising the sun gear drive (244), four identical planetary gears (243), and a ring gear within the socket (241).

Figure 25:
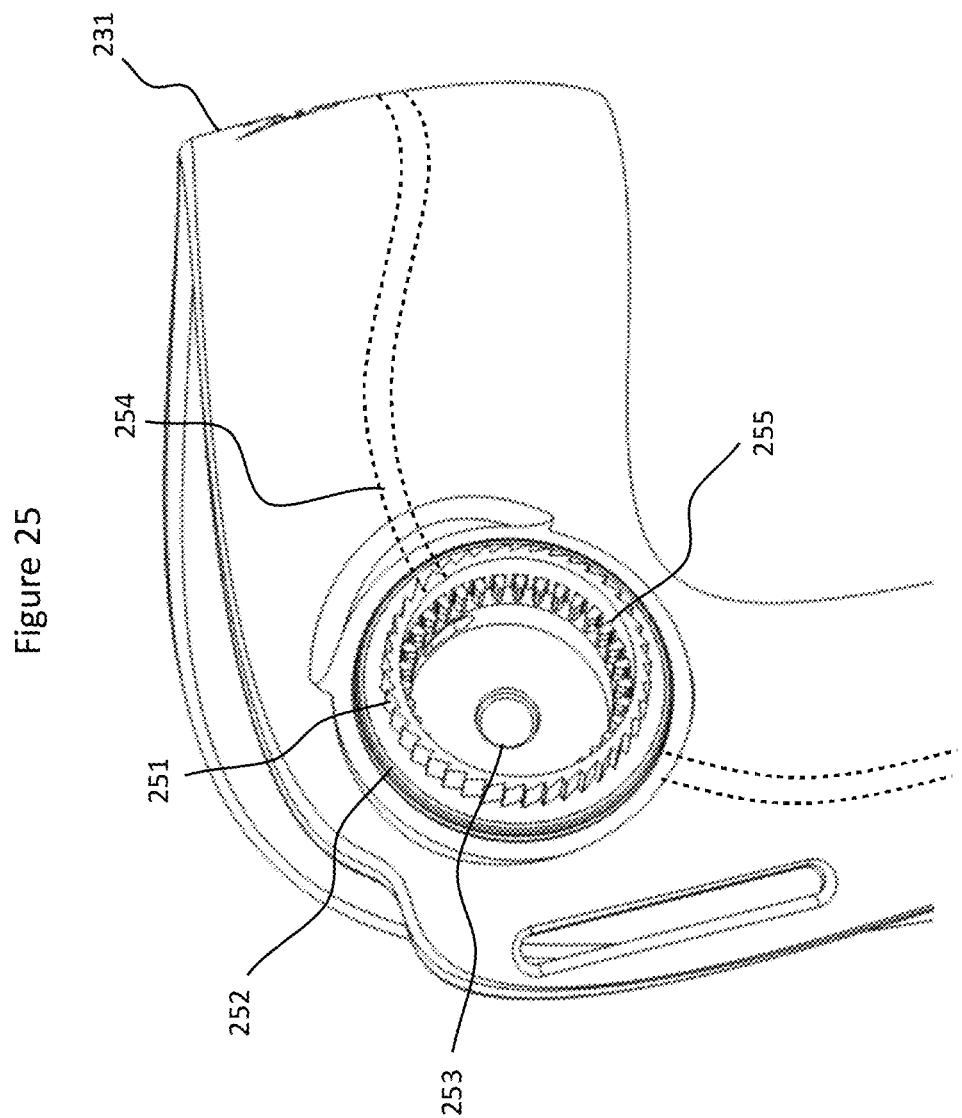
FIG. 25 depicts an embodiment of an adjustable tensioning device according to the invention described herein.

FIG. 25 shows an enlarged side view of the socket (241). The socket—which is integral with the upper frame contributes five critical functions to the operation of the dial tension mechanism. First, there are the mating recesses (251) for the flexible arms of the anti-unspooling mechanism. Second, there is a retaining lip (252) upon which the dial clipped and rotates around. Third, there is a recess (253) for the axial boss of the spool which ensures that the spool is centered and rotates with low friction within the socket. Fourth, there is a tension element guide (254) that provides a pathway for the tensioning element. Fifth, the ring gear (255) is integrated into the socket and contributes to the function of the planetary gear drive.

Figure 26C:
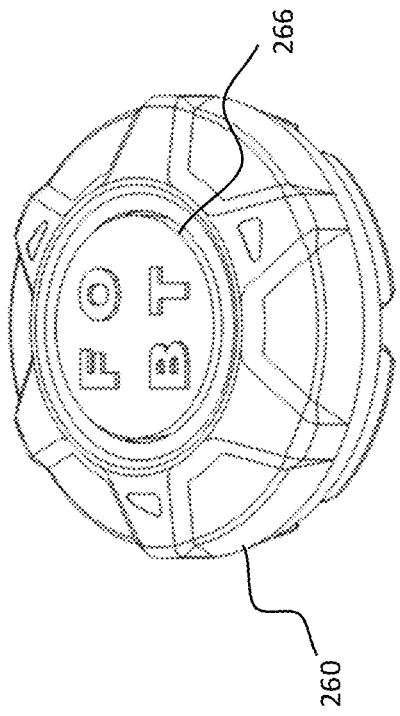
FIGS. 26a, 26b, 26c, and 26d depict aspects of an embodiment of an adjustable tensioning device according to the invention described herein.
Figure 26D:
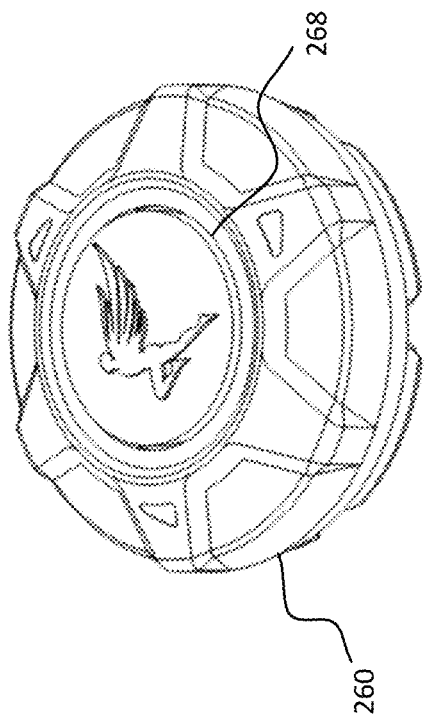
Figure 26A:
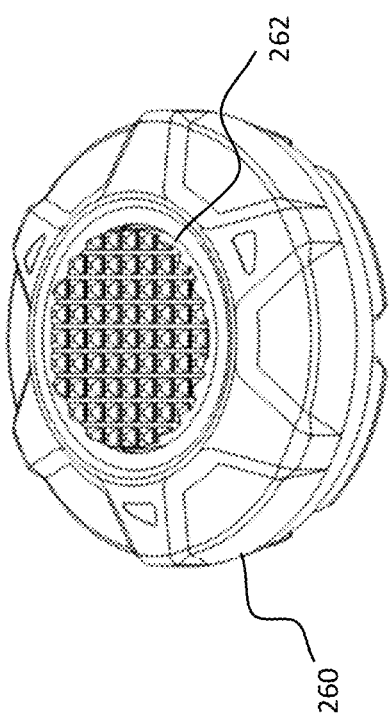
Figure 26B:
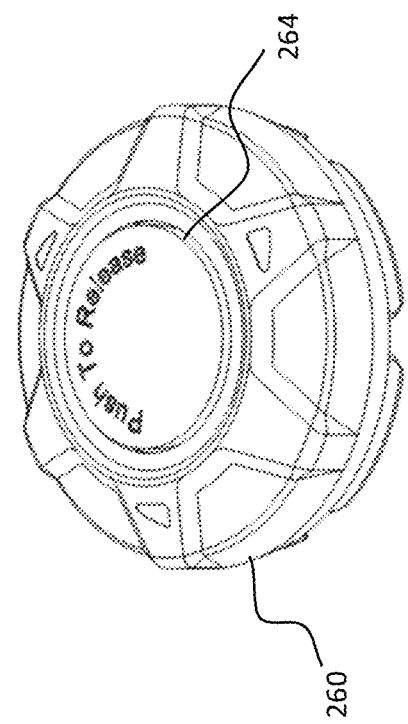

The button and dial of the dial tensioning system are readily visible to the user and can be configured functionally and aesthetically in different ways. The dial may have recesses or grooves to provide a secure grip when the user turns the dial. Additionally, the dial may have a rubberized outer surface or surface features to improve the grip when, for example, the user's hands are wet. In addition to functional benefits, the button and dial may also have branding or ease-of-use benefits. FIG. 26a shows an orthogonal view of a dial (260) and button (262). The button in FIG. 26a is configured with a non-slip surface. FIG. 26b shows an orthogonal view of a dial (260) and a button (264). The button in FIG. 26b is configured with instructions on the operation of the button. In FIG. 26b the marking is recessed into the surface of the button. FIG. 26c shows an orthogonal view of a dial (260) and a button (266). The button in FIG. 26c is configured with a corporate name (in this example, the fictional company "Freight on Board Technologies"). The markings in FIG. 26c are raised above the surface of the button. FIG. 26d shows an orthogonal view of a dial (260) and a button (268). The button in FIG. 26d is configured with a corporate logo (in this example, the emblem of Icarus Medical Innovations of Charlottesville, Virginia).

Applications in Orthotic and Prosthetic Closure Systems

Embodiments of the adjustable tensioning device as described herein have applications for suspension and fitment of orthotic and prosthetic devices, among other wearable devices. Adjustable closure systems offer beneficial function when incorporated into orthotic and prosthetic devices, offering custom fit, function and comfort to meet the patient's specific needs while overcoming common challenges relating to device migration. In some aspects, the adjustable tensioning system may be used in combination with one or more fitting elements. A fitting element can be defined as an interface that adheres or fits a wearable device to the user's limb or body part. Common examples of fitting elements include straps, pads, cushions, laces, load distributors, rigid or semi-rigid panels (also described as leaves), sockets, or sleeves. For example, straps used to don a knee brace or a flexible inner socket to don a prosthetic would be considered fitting elements. In embodiments, the fitting elements are connected to the tensioning elements through a series of channels, guides or anchors. The tensioning elements may be positioned on the interior side (closest to the body part), the exterior side, or internally to the fitting elements. In an embodiment where the fitting element can be a series of panels for the prosthetic socket, the panels line the inner region of a lower-limb prosthetic device. The tensioning element can be a cable that runs circumferentially around the exterior of the panels through guides. By rotating the dial and increasing tension within the tensioning element, the panels can be drawn radially inward, therefore applying a distributed pressure to the user's body part in order to affix the socket to the limb. In aspects, the inner surface of the panels may have a high-friction material such as silicone or a thermoplastic. In other embodiments, the fitting element is a strap for an orthopedic knee brace. The tensioning element can be a lace that is connected to a fabric strap on one end (or wound through the fabric strap) and connected to a rotary dial on the other. By rotating the dial, the lace can be gathered around the spool and the strap is tightened around the user's limb. In other embodiments, the tensioning element may comprise elastic or semi-rigid materials, allowing for a more dynamic or elastic force to be applied to the fitting element.

In embodiments, the fitting element can be comprised of a plurality of overlapping semi-rigid panels, which are pivotally attached at one end. In an example of an adjustable prosthetic socket, the panels can be pivotally attached at the distal end near the base of the prosthetic socket. A series of guides at the proximal end of each overlapping panel provides a path for the tensioning element, in this case a cable. The cable is connected to the spool of a rotary dial, which is located externally on the prosthesis. Upon rotation of the dial, the cable is tensioned and draws the overlapping panels together as well as radially inward. This mechanism provides a relatively uniform, radial force to affix the prosthetic to the user's limb.

Additional Embodiments

In aspects, the tensioning device may further comprise an energy storage element to dynamically adjust forces across, between or around a joint or body part in an orthotic or prosthetic device. may contain individual or interconnected energy storage systems, which control forces around, between or within the joint. The tensile or compression force stored within the energy storage element is controlled by the tensioning device and adjusted by the user as needed. The energy storage element may be a tensioning element or a compression element, or both depending on whether the system is typically under tension or compression during use. In embodiments, the energy storage element may be comprised of elastic bands, springs, liquids (e.g. pneumatic systems) and may also store and release energy in compression as well as tension. The energy storage element may be selected to have specific properties, for example a Young's Modulus that allow for discrete levels of force to be stored and applied around a given axis of the joint. The energy storage system may be connected at one or more points to different regions of the orthosis to direct force around the desired axis. For example, the energy storage element may run across a hinge or a cam in order to generate a torque around a joint rather than providing a force between the joint.

In aspects, the tensioning device is capable of changing the force in a substantially continuous, gradual, incremental, or stepwise manner across a range or spectrum of magnitudes of force. In aspects, it may also be capable of changing the force between an on and off setting, for example where the "on" setting instantly adjusts to the maximum level of force required by the orthotic device and the "off" setting instantly adjusts to zero force sustained by the tensioning device.

In application, the user may require the device to be durable and resistant to environmental wear after years of daily use. Conditions, by example, include exposure to sand, dirt, water, low temperature (below freezing) and high temperature (above 80° F.) periodically or for sustained periods of time. To ensure reliable performance during such conditions for a lifetime of 5 years or more, the tensioning device in aspects may comprise channels in the housing that allow water and debris to be removed from the internal components of the device during washing or operation of the device. In other aspects, the materials may be designed from high-strength, durable plastics or metals that are corrosion resistant, such as stainless steel.

In aspects, multiple systems to generate mechanical advantage, including planetary gears, gear trains and pulleys as described herein may be applied to generate higher degrees of mechanical advantages and overall durability.

In aspects, some or all of the components of the tensioning device may be 3D printed or produced using additive manufacturing methods.

In aspects, different components of the tensioning device can be modular, such that they can be snapped or assembled into place in or on the device. Components may be selected based on the orthotic or prosthetic device, the application, or the user's specific needs. For example, the number, module or size of gears in the planetary gear system can be selected to achieve mechanical advantage between 2:1 and 30:1. Additionally, different knob sizes or geometries may be selected to increase mechanical advantage or improve ergonomics. In aspects, gear systems, gear trains, and/or pulley systems as described herein may be added as an internal component of the orthotic or prosthetic device, incorporated into the orthotic or prosthetic's design and fabrication, or may be added as an external modular attachment to provide a compounding mechanical advantage for the device. In aspects, the orthotic or prosthetic device may comprise more than one tensioning device, for example in the case of a knee-ankle-foot orthosis that requires adjustment of forces around both the knee and ankle joints.

In aspects, the tensioning device may comprise a torque limiting element to prevent torque overload. In such instances, the tensioning device will stop, slip, or disengage when force maintained by the system is above a specific intended amount. Such a feature may also be intentionally designed into the flexible arm system, in which the flexible arms may disengage by design at forces, for example, above 200 lbs. Examples of a torque limiting element include, but are not limited to friction plates, slip-clutches, shear pins, sprocket and sheave mechanisms, synchronous magnetic torque limiters, ball detents, or pawl and spring torque limiters.

In aspects, one or more components of the tensioning device may be electronic or motorized. In other aspects, the tensioning device may further comprise an additional electronic actuator or motor component that winds, unwinds, and/or releases the spool directly or indirectly. For example, the dial component may be paired with a motor, which can be controlled by the user with a digital interface or mobile device in order to rotate the dial and increase, decrease or maintain tension in the orthotic or prosthetic device. In other examples, the electronic or motorized system may be controlled due to sensory input on the orthotic or prosthetic device or on the user. In other aspects, the device may comprise sensors including but not limited to biometric sensors, pressure sensors, tensiometers, accelerometers and goniometers. For example, a closure system, which incorporates the adjustable tensioning system described, may use data from pressure sensors within the fitting elements that interface with the user's body part. As the tensioning system is adjusted to tighten the fitting elements around the body part, the sensors provide a reading of the pressure being applied in order to achieve a target level to secure the device to the body part. In some embodiments, the sensory data may inform the user to increase or decrease the tension applied to optimize fit and function. In other embodiments, the pressure sensors may provide feedback to a motorized adjustment mechanism to increase tension in order to optimize fit and function. A similar outcome may be achieved through a tensiometer that measures tension within the tensioning element itself or within straps used for fitment.

In a particular embodiment, an anchor ring (14) and socket (18) locking geometry described herein and as shown in FIG. 1, which uniquely corresponds to this invention and the orthotic or prosthetic device frame in which it is used. The anchor ring can twist into the socket counter clockwise. When the dial tensioning device is configured to tighten when the dial is rotated in a clockwise direction, the anchor ring self-tightens into the socket when tension is applied to the spool. Four helical threads are positioned around the outer periphery of the anchor ring. Each thread is 8.5 mm tall, having a generally round cross section with a diameter of 4 mm, and a pitch of 110 mm. The threads are symmetrically but not uniformly arranged around the periphery. Each thread is 60 degrees apart from one neighbor and 120 degrees apart from the other neighbor. The inner diameter of the socket is 40 mm. Two fingers on the bottom of the anchor ring deform slightly while the anchor ring is screwed into the socket. When the anchor ring is fully screwed in, the fingers click into corresponding depressions in the socket which prevent the anchor ring from unscrewing. Pins can be inserted into the holes in the depressions to release the fingers thereby allowing the anchor ring to be unscrewed from the socket.

The invention includes the following exemplary embodiments:

An adjustable tensioning device as described herein, wherein the pulley mechanism is built into the orthotic or prosthetic device frame.

The adjustable tensioning device as described herein, further comprising an electronic or motorized component.

The adjustable tensioning device as described herein, further comprising a cylindrical clutch with vertical faces that result in a nearly flat release force that is independent of the lace tension.

The adjustable tensioning device as described herein, further comprising a spool reinforced with metal dowel pins that act as the pivots for the planetary gears and prevent the lace from cutting the spool shaft.

The adjustable tensioning device as described herein, further comprising an anchoring element removably attached to a corresponding socket, wherein the anchoring element is stationary relative to the corresponding socket when tension is applied to the spool.

The adjustable tensioning device as described herein, wherein the anchoring element is lockable.

The adjustable tensioning device as described herein, wherein a sun gear of the planetary gear mechanism has 17 or less teeth; wherein planetary gears of the planetary gear mechanism have six or more teeth; wherein a combination of the sun gear, the planetary gears, and ring gear, provide a torque ratio of at least three-to-one; and wherein the combination of the sun gear, the planetary gears, and the ring gear, generate at least 50 pounds of tension in the tensioning element.

The adjustable tensioning device as described herein, wherein a gear module is comprised of the combination of the sun gear and the planetary gears, and wherein the gear module is about 1.2, the gear height is about 5 mm, and at least one of the sun gear or the planetary gears are made of nylon material.

The adjustable tensioning device as described herein, wherein the anti-unspooling mechanism comprises a system of sprags that stop or limit backlash of the tensioning element, wherein the system of sprags can be released by pressing or rotating the rotatable knob, the release caused by the rotatable knob pushing the sprags of the system of sprags open simultaneously, thereby allowing the spool to unwind the tensioning element.

The adjustable tensioning device as described herein, wherein the spool comprises a pass-through hole allowing tension in the tensioning element to be balanced between both sides of the spool.

The adjustable tensioning device as described herein, wherein dogs or pawls are integrated within the carriage of the planetary gear mechanism.

The adjustable tensioning device as described herein, wherein one or more components are 3D printed.

The adjustable tensioning device as described herein, wherein the adjustable tensioning device is modular, and wherein components are selected or added based on the specific orthotic or prosthetic device, application, or user need.

The adjustable tensioning device as described herein, further comprising an electronic or motorized component.

The adjustable tensioning device as described herein, wherein the device comprises modular components and can be customized to the specific orthotic or prosthetic device, user need, or application through digital design or selection of the modular components during the fabrication process.

While the various embodiments of the tensioning device are described in orthotic and prosthetic devices by example, one skilled in the art will recognize that the same mechanism and features may be applied in other use applications for winding, releasing, and tensioning inelastic or semi-inelastic cable or lace. Such examples include force adjustment in exercise devices, fishing reels, medical device strapping and fitment systems, posture corrective devices, rehabilitative equipment, helmets (including bicycle, military, and athletic helmets), apparel, exoskeletons, pulley systems, and personal protective equipment. The tensioning device may be used in orthotic devices for any joint or body part in order to adjust forces around, between, or within the joint or body part including the knee, ankle, foot, shoulder, elbow, wrist, hand, back, neck, and hip.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all the references cited in this disclosure are each individually incorporated by reference herein in their entirety and as such are intended to provide an efficient way of supplementing the enabling disclosure of this invention as well as provide background detailing the level of ordinary skill in the art. It is noteworthy that in certain embodiments, the reference to an aircraft is utilized. However, such embodiments can be utilized for all types of vehicles where multiple seated individuals are seated one behind the other. It is noteworthy that in certain embodiments the reference to a theater is utilized. However, such embodiments can be utilized for all types of theaters where multiple seated individuals are seated one behind the other.

Although various features of the invention may be described in the context of a single embodiment, the features may also be provided separately or in any suitable combination. Conversely, although the invention may be described herein in the context of separate embodiments for clarity, the invention may also be implemented in a single embodiment.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

"Attachable" as used herein can mean releasably attachable, such as a component that can be attached and then detached, or a component that is attached and remains attached.

In aspects, as used herein, low-sound or low-noise, can be defined as follows. In aspects, sound or noise is quantified in decibels. Whispering has been measured at 30 dB, light rainfall is measured at 40 dB, while a typical refrigerator motor produces about 50 dB. These are all examples of noises that are less than normal conversational noise, which is measured to be around 60 dB. By way of example, the opening of traditional hook and loop, which is too loud for some military applications (e.g., Velcro™) has been measured at about 70 dB. Therefore, for purposes of this Application, "low-noise" or "low-sound" as used herein refers to sound(s) that are less than 60 dB. In aspects, that is the dB measured at around 24 inches from the source of the sound.

As used herein, the term "substantial" and "substantially" refers to what is easily recognizable to one of ordinary skill in the art.

It is to be understood that the phraseology and terminology employed herein is not to be construed as limiting and are for descriptive purpose only.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including," "comprising," "consisting" and grammatical variants thereof do not preclude the addition of one or more components, features, steps, or integers or groups thereof and that the terms are to be construed as specifying components, features, steps or integers.

What is claimed:

1. An adjustable tensioning device comprising:
   a rotatable dial, wherein rotating the rotatable dial causes a spool to turn and a tensioning element to wind around the spool, wherein the spool is configured to store the tensioning element;
   an anti-unspooling mechanism having ratchets and pawls configured to both (a) prevent the tensioning element from unwinding from the spool and (b) prevent the rotatable dial from rotating in more than one direction; and
   a clutch that couples and decouples the rotatable dial from the spool;
   wherein the rotatable dial and the anti-unspooling mechanism remain in constant contact and thereby do not decouple during operation of the adjustable tensioning device, such that the rotatable dial is configured to operationally rotate in only one direction even when the clutch is decoupled from the spool.

2. The adjustable tensioning device of claim 1, wherein the adjustable tensioning device is used to one or more of secure, compress, or tighten, a garment, footwear, equipment, an orthosis, a prosthesis, or apparel, to at least one of a body, a body part, or a body joint.

3. The adjustable tensioning device of claim 1, wherein the adjustable tensioning device is used to tighten or adjust a fit of a garment, footwear, an orthosis, a prosthesis, or apparel.

4. The adjustable tensioning device of claim 1, wherein the adjustable tensioning device is connected to a garment, footwear an orthosis, a prosthesis; or apparel, and wherein the adjustable tensioning device is configured to one or more of increase pressure between the garment, the footwear, the orthosis, the prosthesis, or the apparel and the body part; reduce a distance between the garment, the footwear, the orthosis, the prosthesis, or the apparel and the body part; move the garment, the footwear, the orthosis, the prosthesis, or the apparel radially towards the body part; or tighten the garment, the footwear, the orthosis, the prosthesis, or the apparel around the body part.

5. The adjustable tensioning device of claim 1, wherein the single direction of rotation is to wind the tensioning element around the spool.

6. The adjustable tensioning device of claim 1, wherein the rotatable dial is rotated using at least one of a motor, an actuator, or a controller.

7. The adjustable tensioning device of claim 1, wherein the adjustable tensioning device is an element of a closure system.

8. The adjustable tensioning device of claim 7, wherein the closure system comprises one or more straps, one or more pressure plates, one or more load distributors, one or more pads, or one or more sockets.

9. The adjustable tensioning device of claim 7, wherein the closure system comprises one or more guides, one or more anchors, or one or more channels, located in or on the closure system, and wherein the tensioning element passes through the one or more guides, one or more anchors, or one or more channels to direct a location of adjustable pressure applied by the closure system to the body part.

10. The adjustable tensioning device of claim 7, further comprising a motor, an actuator, and one or more sensors, wherein an adjustment is controlled by the motor based on information from the one or more sensors.

11. The adjustable tensioning device of claim 10, wherein the one or more of the one or more sensors is a pressure sensor, a tensiometer, or combinations thereof.

12. The adjustable tensioning device of claim 1, further comprising a plurality of overlapping panels, the plurality of overlapping panels pivotally attached to each other at ends of the plurality of overlapping panels, and one or more guide or channel connected to at least two of the plurality of overlapping panels, wherein the tensioning element is guided through the one or more guide or channel, and wherein when the tensioning element is wound around the winding element, the plurality of overlapping panels apply a pressure to the body part, reduce a distance between the device and the body part, move the device radially inward towards the body part, or tighten the device around the body part.

13. The adjustable tensioning device of claim 1, wherein the clutch comprises a first clutch element and a second clutch element, wherein the tensioning element is allowed to unwind from the spool using a push button, wherein pressing the push button causes the first clutch element to operationally decouple from the second clutch element.

14. An adjustable tensioning device comprising:
a rotatable dial, wherein rotating the rotatable dial causes a spool to turn and a tensioning element to wind around the spool, wherein the spool is configured to store four or more inches of the tensioning element;
an anti-unspooling mechanism to (a) prevent the tensioning element from unwinding from the spool and (b) prevent the rotatable dial from rotating in more than one direction; and
a clutch that couples and decouples the rotatable dial from the spool wherein the clutch comprises two elements, a first clutch element comprising a plurality of protrusions, and a second clutch element comprising a plurality of recesses, wherein the plurality of protrusions of the first clutch element intermesh with the plurality of recesses of the second clutch element;
wherein the rotatable dial does not decouple from the anti-unspooling mechanism, and wherein the rotatable dial is configured to operationally rotate in only one direction even when the clutch is decoupled from the spool.

15. The adjustable tensioning device of claim 14, wherein the first clutch element is disengaged from the second clutch element by pushing a button.

16. The adjustable tensioning device of claim 14, wherein the rotatable dial that does not decouple from the anti-unspooling mechanism is permanently coupled to the anti-unspooling mechanism.

17. The adjustable tensioning device of claim 14, wherein the anti-unspooling mechanism to prevent the tensioning element from unwinding from the spool is capable of having a tension acting on the spool of about 50 pounds or more.

18. The adjustable tensioning device of claim 14, wherein the rotatable dial is decoupled from the spool by sliding the first clutch element past the second clutch element, and wherein a force to decouple the rotatable dial from the spool is less than 10 pounds when a force on the tensioning element is 100 lbs.

19. The adjustable tensioning device of claim 14, wherein the rotatable dial is decoupled from the spool by sliding the first clutch element past the second clutch element, and wherein a force to decouple the rotatable dial from the spool, versus a force on the tensioning element, increases by less than 0.5 pounds/per pound of force of tension in the tensioning element.

20. The adjustable tensioning device of claim 14, further comprising a multiplying system comprising a first planetary gear mechanism and a second planetary gear mechanism, wherein a sun gear of the second planetary gear mechanism is driven by a carriage of the first planetary gear mechanism.

21. The adjustable tensioning device of claim 20, wherein one or both of the first planetary gear mechanism and the second planetary gear mechanism comprise a sun gear, two or more planetary gears, a ring gear, and a carriage upon which the two or more planetary gears are carried.

22. An adjustable tensioning device comprising:
a rotatable dial, wherein rotating the rotatable dial causes a spool to turn and a tensioning element to wind around the spool, wherein the spool is configured to store four or more inches of the tensioning element;
a torque multiplying system, wherein the torque multiplying system is capable of increasing the force applied to the tensioning element by three times or more;
an anti-unspooling mechanism to prevent the tensioning element from unwinding from the spool, wherein the anti-unspooling mechanism does not decouple from the rotatable dial; and a clutch that couples and decouples the rotatable dial from the spool;

wherein the spool includes a bottom flange and a top flange, wherein one or more reinforcement structures are located within the spool and oriented perpendicular to the bottom flange and the top flange and parallel to an axis of rotation of the spool; and wherein the rotatable dial is configured to operationally rotate in only one direction even when the clutch is decoupled from the spool.

23. The adjustable tensioning device of claim 22, wherein the torque multiplying system comprises one or more planetary gear mechanisms, and the at least one of the one or more reinforcement structures is a shaft for at least one planetary gear of the one or more planetary gear mechanism.

24. A low-noise adjustable tensioning device comprising:
a rotatable dial, wherein rotating the rotatable dial causes a spool to turn and a tensioning element to wind around the spool, wherein the spool is configured to store four or more inches of the tensioning element; and an anti-unspooling mechanism to prevent the tensioning element from unwinding from the spool, the anti-unspooling mechanism comprising a one-way roller bearing clutch, a sprag clutch, angled metal flexible arms or vanes, or combinations thereof;

wherein the rotatable dial and the anti-unspooling mechanism remain in constant contact and thereby do not decouple during operation of the low-noise adjustable tensioning device, such that the rotatable dial is configured to operationally rotate in only one direction even when the anti-unspooling mechanism is decoupled from the spool.

25. The adjustable tensioning device of claim 24, wherein distal tips of the flexible arms or vanes dig into and/or engage with a corresponding wall of the anti-unspooling mechanism to prevent counter rotation.

26. The adjustable tensioning device of claim 24, further comprising a torque multiplying; mechanism.

27. The adjustable tensioning device of claim 24, wherein the device is, or is attached to, an orthosis or a prosthesis.

* * * * *